US012364696B2

(12) United States Patent
Sinclair et al.

(10) Patent No.: US 12,364,696 B2
(45) Date of Patent: Jul. 22, 2025

(54) TREATMENT OF AUTOIMMUNE DISEASE

(71) Applicant: JAK Slave Pty Ltd, Surrey Hills (AU)

(72) Inventors: Rodney Sinclair, East Melbourne (AU); Yuk-Shui Andrew Lau, Doncaster (AU)

(73) Assignee: JAK Slave Pty Ltd, Surrrey Hills (AU)

( * ) Notice: Subject to any disclaimer, the term of this patent is extended or adjusted under 35 U.S.C. 154(b) by 784 days.

(21) Appl. No.: 17/434,241

(22) PCT Filed: Feb. 27, 2020

(86) PCT No.: PCT/AU2020/050175
§ 371 (c)(1),
(2) Date: Aug. 26, 2021

(87) PCT Pub. No.: WO2020/172714
PCT Pub. Date: Sep. 3, 2020

(65) Prior Publication Data
US 2022/0143025 A1    May 12, 2022

Related U.S. Application Data

(60) Provisional application No. 62/811,353, filed on Feb. 27, 2019.

(51) Int. Cl.
*A61K 31/519*    (2006.01)
*A61K 9/00*    (2006.01)
*A61P 17/14*    (2006.01)

(52) U.S. Cl.
CPC ............ *A61K 31/519* (2013.01); *A61K 9/006* (2013.01); *A61P 17/14* (2018.01)

(58) Field of Classification Search
CPC .................................................. A61K 31/519
See application file for complete search history.

(56) References Cited

U.S. PATENT DOCUMENTS 9,198,911 B2    12/2015    Christiano et al.
9,730,877 B2    8/2017    Christiano et al.

FOREIGN PATENT DOCUMENTS

| CN | 107441054 | 12/2017 |
| WO | 2001/042246 | 6/2001 |
| WO | 2002/085304 | 10/2002 |
| WO | 2002/096909 | 12/2002 |
| WO | 2003/048162 | 6/2003 |
| WO | 2004/054546 | 7/2004 |
| WO | 2006/089082 | 8/2006 |
| WO | 2014/016396 | 1/2014 |
| WO | 2014/071105 | 5/2014 |
| WO | 2017/153822 | 9/2017 |
| WO | 2019/010535 | 1/2019 |

OTHER PUBLICATIONS

Messenger, et al. British Journal of Dermatology 2004; 150, 186-194.*
Acikgoz et al., (2014) "The effect of oral cyclosporine in the treatment of severe alopecia areata", Cutan Ocul Toxicol, 33(3):247-252.
Almutairi et al., (2019) "Janus Kinase Inhibitors for the Treatment of Severe Alopecia Areata: An Open-Label Comparative Study", Dermatology, 1-7.
Amin et al., (2015) "Oral Film Technology: Challenges and Future Scope for Pharmaceutical Industry", Human Journals, 3(3):183-203.
Bittencourt et al., (2014) "Chronic telogen effluvium and female pattern hair loss are separate and distinct forms of alopecia: a histomorphometric and immunohistochemical analysis", Clinical and Experimental Dermatology, 868-873.
Craiglow et al., (2017) "Tofacitinib for the treatment of alopecia areata and variants in adolescents.", Journal of the American Academy Dermatology., 76(1):29-32.
Crispin et al., (2016) "Safety and efficacy of the JAK inhibitor tofacitinib citrate in patients with alopecia areata", JCI Insight, 1(15):e89776, 1-11. rcvd clt email dtd Jan. 16, 2022.
Dey, Paramita and Maiti, Sabyasachi., (2010) "Orodispersible tablets: A new trend in drug delivery", 1(1):1-4.
Dowty et al., (2014) "The Pharmacokinetics, Metabolism, and Clearance Mechanisms of Tofacitinib, a Janus Kinase Inhibitor, in Humans", Drug Metab Dispos, 42:759-773.
Irfan et al., (2016) "Orally disintegrating films: A modern expansion in drug delivery system", Saudi Pharmaceutical Journal, 24:537-546.
Jabbari et al., (2016) "Treatment of an alopecia areata patient with tofacitinib results in regrowth of hair and changes In serum and skin biomarkers.", Exp Dermatol., 25(8):642-643.
Jabbari et al., (2018) "An Open-Label Pilot Study to Evaluate the Efficacy of Tofacitinib in Moderate to Severe Patch-Type Alopecia Areata, Totalis, and Universalis.", The Journal of Investigative Dermatology, 138(7):1539-1545.
Jamroz et al., (2017) "3D Printed Orodispersible Films With Aripiprazole", ResearchGate, 1-2.
Jiao et al., (2018) "Oral administration of short chain fatty acids could attenuate fat deposition of pigs", PLoS ONE, 13 (5):e0196867, 1-12.
JNS.org., (2015) "Israeli-developed cancer drug found to effectively treat autoimmune baldness", JNS.org, 1-3.
Kerkemeyer et al., (2019), J Am Acad Dermatol, 1228-1230.

(Continued)

*Primary Examiner* — Shawquia Jackson
(74) *Attorney, Agent, or Firm* — Mandar A. Joshi; Bozicevic, Field & Francis LLP

(57) ABSTRACT

The present invention relates to methods and compositions for the treatment of autoimmune diseases and of excessive hair shedding or hair loss in a subject or for promoting hair growth in a subject wherein the subject has an autoimmune hair loss disorder, such as alopecia areata. The methods and compositions comprise the administration of a janus kinase inhibitor, such as tofacitinib, wherein the inhibitor is predominantly absorbed through the oral mucosal routes such as the sublingual mucosa.

18 Claims, 10 Drawing Sheets

(56) References Cited

OTHER PUBLICATIONS

Lai et al., (2019) "Cyclosporine for moderate-to-severe alopecia areata: A double-blind, randomized, placebo-controlled clinical trial of efficacy and safety", J Am Acad Dermatol, 1-8.
Lai et al., (2019) "Systemic treatments for alopecia areata: A systematic review", The Australasian College of Dermatologists, 1-13.
Lai et al., (2021) "Sublingual tofacitinib for alopecia areata: a roll-over pilot clinical trial and analysis of pharmacokinetics", the International Society of Dermatology, 1-5.
Lamba et al., (2016) "Extended-Release Once-Daily Formulation of Tofacitinib: Evaluation of Pharmacokinetics Compared With Immediate-Release Tofacitinib and Impact of Food", The Journal of Clinical Pharmacology, 56 (11):1362-1371.
Liu et al., (2017) "Tofacitinib for the treatment of severe alopecia areata and variants: A study of 90 patients.", Journal of the American Academy Dermatology., 76(1):22-28.
Merk et al., (1987) "Human Hair Follicle Benzo[a]pyrene and Benzo[a]pyrene 7,8-diol Metabolisll1: Effect of Exposure to a Coal Tar Containing Shampoo", The Society for Investigative Dermatology. Inc., 71-76.
Messenger, A.G. and Sinclair, R., (2006) "Follicular miniaturization in female pattern hair loss: clinicopathological correlations", British Journal of Dermatology, 155:926-930.
Nagaraju et al., (2013) "Comprehensive Review On Oral Disintegrating Films", Current Drug Delivery, 10:96-108.
Narang, Neha and Sharma, Jyoti, (2001) "Sublingual Mucosa as a Route for Systemic Drug Delivery", Int J Pharm Pharm Sci, 3(2):18-22.
Olsen et al., (1997), Hair and Nails, p. 20.
Olsen et al., (1999) "Alopecia areata investigational assessment guidelines*", Journal of the American Academy of Dermatology, 40(2):242-243.
Olsen et al., (2004) "Alopecia areata investigational assessment guidelines—Part II", J Am Acad Dermatol, 51 (3):440-447.
Olsen et al., (2016), J Am Acad Dermatol, 1268-1270.
Pond, Susan M. and Tozer, Thomas N., (1984) "First-pass elimination. Basic concepts and clinical consequences.", Clinical Pharmacokinetics., 9(1):1-25.
Ramos et al., (2019) "Minoxidil 1 mg oral versus minoxidil 5% topical solution for the treatment of female-pattern hair oss: A randomized clinical trial", J Am Acad Dermtol, 82(1):252-253.
Ramos et al., (2020) "Sulfotransferase activity in plucked hair follicles predicts response to topical minoxidil treatment in Brazilian female pattern hair loss patients", ResearchGate, 1-7.
Sayeed, Vilayat and Ashraf, Muhammad, (2014) "Considerations in Developing Sublingual Tablets—An Overview", PharmTech, 1-11.
Shi et al., (2012) "The Effect of CYP3A4 Inhibition or Induction on the Pharmacokinetics and Pharmacodynamics of Orally Administered Ruxolitinib (INCB018424 Phosphate) in Healthy Volunteers", Journal of Clinical Pharmacology, 52:809-818.
Singh et al., (2012) "An Overview on fast Disintegrating Sublingual Tablets", International Journal of Drug Delivery, 4 (4):407-417.
Wang et al., (2018) "JAK Inhibitors for Treatment of Alopecia Areata.", J Invest Dermatol., 138(9):1911-1916.
Xing et al., (2014) "Alopecia areata is driven by cytotoxic T lymphocytes and is reversed by JAK inhibition.", Nat Med., 20(9):1043-1049.
"Xeljanz (Tofacitinib Citrate): My experience on the trial", (2014);1-6.
Yang et al., (2018) "Tofacitinib for the treatment of lichen planopilaris: A case series", Wiley Dermatologic Therapy, 1-4.
Reisfield et al., (2007) "Rational Use of Sublingual Opioids in Palliative Medicine", Journal of Palliative Medicine, 10(2):465-475.
Label for XELJANZ/XELJANZ XR (tofacitinib tablets), (2018) "XELJANZ/XELJANZ XR is indicated for the treatment of adult patients with moderately to severely active rheumatoid arthritis who have had an inadequate response or intolerance to methotrexate. It may be used as monotherapy or in combination with methotrexate or other nonbiologic disease-modifying antirheumatic drugs (DMARDs).", Pfizer Labs, pp. 1-52.

* cited by examiner

A

B

TREATMENT OF AUTOIMMUNE DISEASE

TECHNICAL FIELD

The present invention relates to methods and compositions for treatment of autoimmune disease in a subject. The present invention relates to methods and compositions for treatment of excessive hair shedding or hair loss in a subject or for promoting hair growth in a subject.

BACKGROUND

Hair follicles on the scalp do not continuously produce hair. They cycle through a growth stage that can last two or more years, then regress to a resting stage for up to three months before starting to grow a new hair fiber again. At any time on a healthy human scalp, about 80% to 90% of the hair follicles are growing hair. These active follicles are in what is called the anagen phase. That leaves up to 10% to 20% percent of scalp hair follicles in a resting state called telogen, when they don't produce any hair fiber. Changes in actual amount of hair fall occur in number of hair loss conditions including for example anagen effluvium, chemotherapy induced hair loss, acute and chronic telogen effluvium, alopecia areata, cicatricial alopecia, male pattern hair loss (MPHL) and female pattern hair loss (FPHL).

Men commonly complain of increased hair loss or hair shedding, especially after washing their hair. Changes in actual amount of hair fall occur in number of hair loss conditions including anagen effluvium, chemotherapy induced hair loss, acute and chronic telogen effluvium, alopecia areata, cicatricial alopecia and male pattern hair loss (MPHL).

Female pattern hair loss (FPHL) is the most common cause of hair loss encountered in clinical practice for women (Messenger et al. 2010). FPHL is a complex polygenic disorder characterised clinically by diffuse hair thinning over the mid frontal scalp and histologically by hair follicle miniaturization. The proportion of miniaturized follicles increases with the severity of hair loss (Messenger et al. 2006). FPHL adversely impacts quality of life and the prevalence of FPHL increases with age. In a population study of over 700 women, FPHL was found in 12% of women aged 20-29 and 57% of women aged >80. Hair loss severity also increases with age.

There are creams and lotions available for the treatment of hair loss and hair shedding disorders which can often leave hair look oily which is undesirable.

There is a requirement for new treatments for conditions of hair loss and excessive hair shedding, autoimmune disease and for the promotion of hair growth (including increasing hair length and beard growth).

SUMMARY

The present invention relates to methods and compositions for the treatment of autoimmune disease in a subject by administration of a dose of JAK inhibitor absorbed through the oral mucosa, preferably, through the sublingual mucosa.

The present invention relates to methods and compositions for the treatment of hair loss or excessive hair shedding in a subject or for promoting hair growth in a subject by administration of a dose of JAK inhibitor absorbed through the oral mucosa, preferably, through the sublingual mucosa. Such compositions are easy to administer and likely to achieve increased patient compliance compared to traditional treatments i.e. such as tablets which are absorbed in the lower gastrointestinal tract and thus must be swallowed by patients and topical lotions which can leave hair looking oily or negatively impact on the look and feel of the hair.

In an aspect, the present invention provides a method of treating hair loss or excessive hair shedding in a subject or for promoting hair growth in a subject by administering to a subject an effective dose of a janus kinase inhibitor (JAK) inhibitor that is predominantly absorbed through the oral mucosa.

In an embodiment, the present invention provides a method of treating autoimmune disease in a subject by administering to a subject an effective dose of a janus kinase inhibitor (JAK) inhibitor that is predominantly absorbed through the oral mucosa.

In an embodiment, the present invention provides a method of treating hair loss in a subject by administering to a subject an effective dose of a janus kinase inhibitor (JAK) inhibitor that is predominantly absorbed through the oral mucosa.

In an aspect, the present invention provides a method of treating excessive hair shedding in a subject by administering to a subject an effective dose of a janus kinase inhibitor (JAK) inhibitor that is predominantly absorbed through the oral mucosa.

In an aspect, the present invention provides a method of promoting hair growth in a subject by administering to a subject an effective dose of a janus kinase inhibitor (JAK) inhibitor that is predominantly absorbed through the oral mucosa.

In an embodiment, the oral mucosa is the sublingual mucosa.

In an embodiment, the JAK inhibitor is tofacitinib. In an embodiment, tofacitinib is tofacitinib citrate.

In an embodiment, the dose comprises a sublingual adhesion agent.

In an embodiment, tofacitinib is in the range of from about 0.1 mg to 50 mg, or from about 0.1 mg to 40 mg, or from about 0.1 mg to 30 mg, or from about 0.1 mg to 20 mg, or from about 0.1 mg to 18 mg, or from about 1.5 mg to 15 mg, or from about 0.2 mg to 12.5 mg, or from about 0.2 mg to 10 mg, or from about 0.5 mg to 8 mg, or from about 1 mg to 6 mg, or from about 1 mg to 5 mg, or from about 1 mg to 4 mg, or from about 1 mg to 3 mg, or from about 1 mg to 2 mg, or is about 5 mg, or is about 4 mg, or is about 3 mg, or is about 2 mg, or is about 0.5 mg daily.

In an embodiment, the dose is administered at least every 3 days, at least every 2 days, or daily. In an embodiment, the dose is administered daily.

In an embodiment, the dose is in a form selected from a: strip, wafer, pellet, film, troche, tablet, lipid matrix tablet, capsule, pill, granule, pellet, powder, drop, spray and lozenge. In an embodiment, the dose is a strip. In an embodiment, the dose is a wafer. In an embodiment, the dose is a film.

In an embodiment, the method further comprises administering one or more of a: (i) further JAK inhibitor, (ii) vasodilator, (iii) aldosterone antagonist, (iv) 5α-reductase inhibitor, (v) non-steroidal antiandrogen drug, (vi) steroidal antiandrogen, (vii) prostaglandin D2 receptor antagonist, (viii) immunosuppressant, and (ix) glucocorticoid.

In an embodiment, the method further comprises administering one or more of: (i) a further JAK inhibitor in the range of from about 0.1 mg to 50 mg; (ii) minoxidil in the range of from about 0.1 mg to 20 mg; (iii) spironolactone in the range of from about 10 mg to 500 mg; (iv) finasteride in the range of from about 0.1 mg to 1 mg; (v) dutasteride in the range of from about 0.01 mg to 1 mg; (vi) flutamide in the range of from about 10 mg to 500 mg; (vii) cyproterone acetate in the range of from about 1 mg to 100 mg; (viii) bicalutamide in the range of from about 1 mg to 100 mg; (xi) enzalutamide in the range of from about 1 mg to 100 mg; (x) nilutamide in the range of from about 1 mg to 100 mg; (xi) drosperidone in the range of from about 0.1 mg to 10 mg; (xii) apalutamide in the range of from about 1 mg to 100 mg; (xiii) buseralin in the range of from about 0.1 mg to 10 mg; (xiv) setipiprant in the range of from about 50 mg to 4000 mg; (xv) fevipiprant in the range of from about 50 mg to 1000 mg; (xvi) cyclosporin in the range of from about 10 mg to 600 mg; (xvii) methotrexate in the range of from about 2.5 mg to 40 mg; (xviii) azathioprine in the range of from about 25 mg to 200 mg; (xix) prednisolone in the range of from about 0.1 mg to 40 mg; and (xx) dexamethasone in the range of from about 0.1 mg to 5 mg. In an embodiment, the further JAK inhibitor is selected from baricitinib and ruxolitinib. In an embodiment, baricitinib is in the range of from about 0.1 mg to 4 mg. In an embodiment, ruxolitinib is in the range of from about 0.1 mg to 40 mg.

In an embodiment, the hair loss or excessive hair shedding is the result of one or more of the following: alopecia areata, alopecia totalis, alopecia universalis, androgenetic alopecia, hair follicle miniaturization, telogen effluvium, anagen effluvium, chemotherapy induced hair loss, male pattern baldness, female pattern baldness, monilethrix, thyroid problems, anaemia, polycystic ovary syndrome, cicatricial alopecia, congenital hypotrichosis, loose anagen hair syndrome, hypotrichosis, malnutrition, folliculitis decalvans, tufted folliculitis, alopecia planopilaris, frontal fibrosing alopecia, lichen planopilaris, lichen planopilaris and lichen frontal fibrosing. In an embodiment, the hair loss or excessive hair shedding is the result of alopecia areata.

In an embodiment, cicatricial alopecia comprises one or more of lichen planopilaris, discoid lupus erythematosus, and folliculitis decalvans.

In an embodiment, hair loss or excessive hair shedding is the result of alopecia areata. In an embodiment, the alopecia areata is mild alopecia areata. In an embodiment, the alopecia areata is moderate alopecia areata. In an embodiment, the alopecia areata is severe alopecia areata. In an embodiment, the alopecia areata is treatment resistant alopecia areata.

In an embodiment, promoting hair growth comprises promoting scalp hair growth in a subject. In an embodiment, promoting hair growth comprises promoting beard growth in a subject. In an embodiment, promoting hair growth comprises promoting eyebrow growth in a subject. In an embodiment, promoting hair growth comprises promoting eyelash growth in a subject. In an embodiment, promoting hair growth comprises increasing hair length in a subject.

In an aspect, the present invention provides an oral composition predominantly absorbed through the oral mucosa for treating hair loss or excessive hair shedding in a subject or for promoting hair growth in a subject comprising a JAK inhibitor.

In an embodiment, the JAK inhibitor is in the range of from about 0.1 to about 50 mg.

In an embodiment, the JAK inhibitor is in the range of from about 0.1 to about 20 mg.

In an embodiment, tofacitinib is in the range of from about 0.1 to about 20 mg.

In an embodiment, the oral composition is a sublingual composition predominantly absorbed through the sublingual mucosa.

In an embodiment, the JAK inhibitor is tofacitinib. In an embodiment, tofacitinib is in the range of from about 0.1 mg to 50 mg, or from about 0.1 mg to 40 mg, or from about 0.1 mg to 30 mg, or from about 0.1 mg to 20 mg, or from about 0.1 mg to 18 mg, or from about 0.1 mg to 15 mg, or from about 0.2 mg to 12.5 mg, or from about 0.2 mg to 10 mg, or from about 0.5 mg to 8 mg, or from about 1 mg to 6 mg, or from about 1 mg to 5 mg, or from about 1 mg to 4 mg, or from about 1 mg to 3 mg, or from about 1 mg to 2 mg, or is about 5 mg, or is about 4 mg, or is about 3 mg, or is about 2 mg, or is about 1 mg, or is about 0.5 mg daily.

In an embodiment, the composition additionally comprises one or more of: (i) a further JAK inhibitor in the range of from about 0.1 mg to 50 mg; (ii) minoxidil in the range of from about 0.1 mg to 20 mg; (iii) spironolactone in the range of from about 10 mg to 500 mg; (iv) finasteride in the range of from about 0.1 mg to 1 mg; (v) dutasteride in the range of from about 0.01 mg to 1 mg; (vi) flutamide in the range of from about 10 mg to 500 mg; (vii) cyproterone acetate in the range of from about 1 mg to 100 mg; (viii) bicalutamide in the range of from about 1 mg to 100 mg; (ix) enzalutamide in the range of from about 1 mg to 100 mg; (x) nilutamide in the range of from about 1 mg to 100 mg; (xi) drosperidone in the range of from about 0.1 mg to 10 mg; (xii) apalutamide in the range of from about 1 mg to 100 mg; (xiii) buseralin in the range of from about 0.1 mg to 10 mg; (xiv) setipiprant in the range of from about 50 mg to 4000 mg; (xv) fevipiprant in the range of from about 50 mg to 1000 mg; (xvi) cyclosporin in the range of from about 10 mg to 600 mg; (xvii) methotrexate in the range of from about 2.5 mg to 40 mg; (xviii) azathioprine in the range of from about 25 mg to 200 mg; (xix) prednisolone in the range of from about 0.1 mg to 40 mg; and (xx) dexamethasone in the range of from about 0.1 mg to 5 mg.

In an embodiment, the composition additionally comprises minoxidil in the range of from about 0.1 mg to 20 mg.

In an embodiment, the further JAK inhibitor is selected from baricitinib and ruxolitinib. In an embodiment, baricitinib is in the range of from about 0.1 mg to 4 mg. In an embodiment, ruxolitinib is in the range of from about 0.1 mg to 40 mg.

In an embodiment, the composition comprises a sublingual adhesion agent. In an embodiment, the composition comprises a disintegration agent which aids disintegration of the composition in the presence of saliva. In an embodiment, the composition comprises a taste modifying agent.

In an embodiment, the composition is in a form selected from a: strip, wafer, pellet, film, troche, tablet, lipid matrix tablet, capsule, pill, granule, pellet, powder, drop, spray and lozenge. In an embodiment, the composition is in a form selected from a: strip, wafer, and film.

In an aspect, the present invention provides a composition for treating hair loss or excessive hair shedding in a subject or for promoting hair growth in a subject comprising a JAK inhibitor and minoxidil. In an embodiment, the composition is orally administered. In an embodiment, the composition is predominantly absorbed through the oral mucosa. In an embodiment, the composition is predominantly absorbed through the sublingual mucosa. In an embodiment, the concentration of the JAK inhibitor is in the range of from about 0.1 mg to 50 mg. In an embodiment, the JAK inhibitor is tofacitinib. In an embodiment, the concentration of minoxidil is in the range of from about 0.1 mg to 20 mg.

In an aspect, the present invention provides a sublingual composition for treating hair loss or excessive hair shedding in a subject or for promoting hair growth in a subject comprising tofacitinib and minoxidil.

In an aspect, the present invention provides use of a JAK inhibitor in the preparation of a medicament for the treatment of autoimmune disease, hair loss or excessive hair shedding in a subject or for promoting hair growth in a subject by administering to a subject an effective dose of a JAK inhibitor through the sublingual mucosa.

In an aspect, the present invention provides use of tofacitinib in the preparation of a medicament for the treatment of autoimmune disease, hair loss or excessive hair shedding in a subject or for promoting hair growth in a subject by administering to a subject an effective dose of tofacitinib through the oral mucosa.

In an aspect, the present invention provides use of tofacitinib in the preparation of a medicament for the treatment of autoimmune disease, hair loss or excessive hair shedding in a subject or for promoting hair growth in a subject by administering to a subject an effective dose of tofacitinib through the sublingual mucosa.

In an aspect, the present invention provides an oral composition predominantly absorbed through the oral mucosa for treating autoimmune disease in a subject comprising a JAK inhibitor.

In an aspect, the present invention provides use of a JAK inhibitor in the preparation of a medicament for the treatment of autoimmune disease in a subject or for promoting hair growth in a subject by administering to a subject an effective dose of a JAK inhibitor through the sublingual mucosa.

In an aspect, the present invention provides use of tofacitinib in the preparation of a medicament for the treatment of autoimmune disease in a subject or for promoting hair growth in a subject by administering to a subject an effective dose of tofacitinib through the oral mucosa.

In an aspect, the present invention provides use of tofacitinib in the preparation of a medicament for the treatment of autoimmune disease in a subject by administering to a subject an effective dose of tofacitinib through the sublingual mucosa.

In an embodiment, the autoimmune disease is selected from rheumatoid arthritis, psoriasis, psoriatic arthritis, vitiligo, sarcoid, atopic dermatitis, ulcerative colitis, lupus erythematosus, lichen planus, Hashimoto's disease, Graves' disease, Crohn's disease, alopecia and alopecia areata.

Any embodiment herein shall be taken to apply mutatis mutandis to any other embodiment unless specifically stated otherwise. For instance, as the skilled person would understand examples of JAK inhibitors outlined for compositions of the invention equally apply to the methods of the invention.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

DESCRIPTION OF EMBODIMENTS

Figure 1:
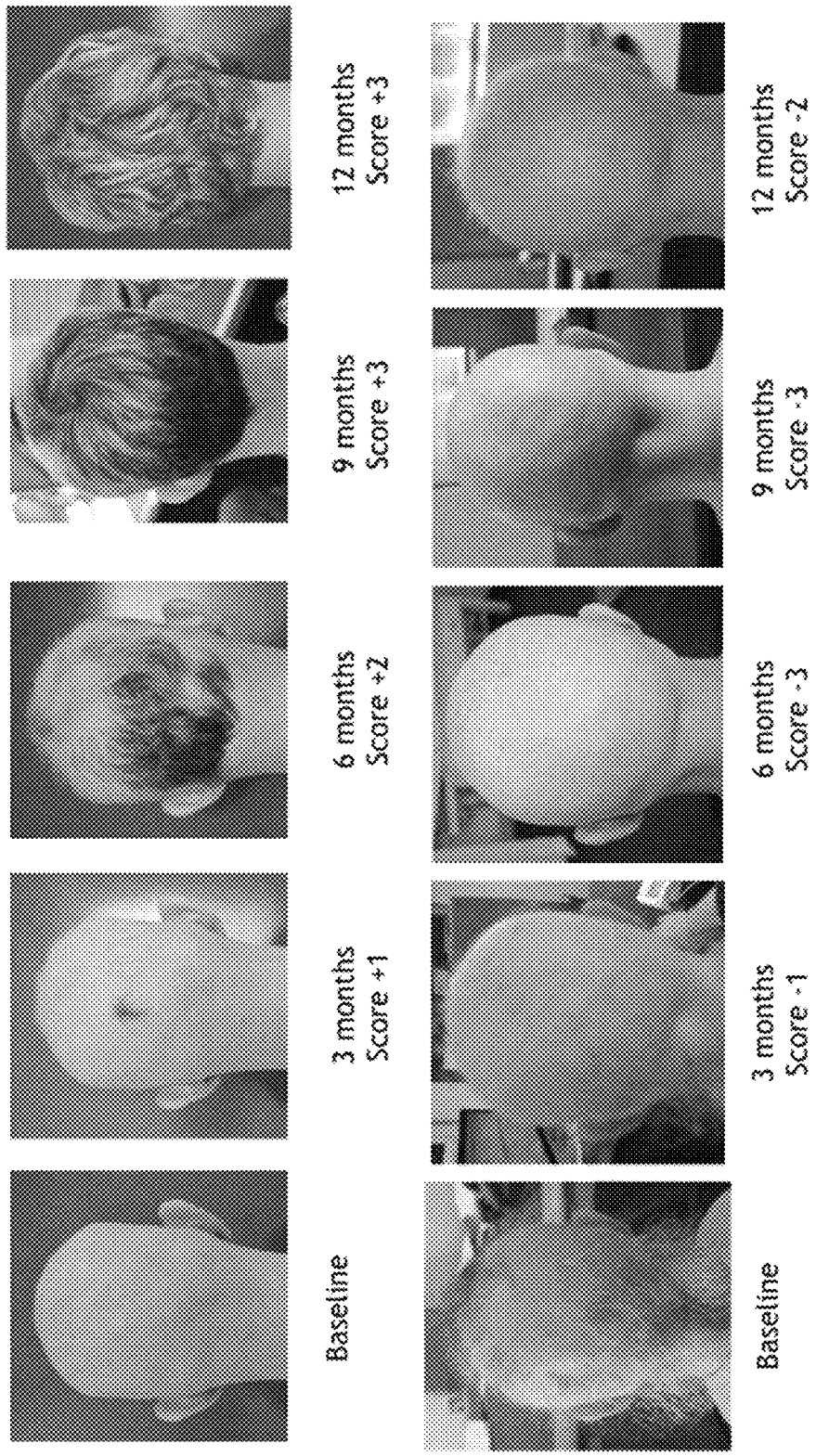
FIG. 1: Shows examples of photos of hair regrowth and the correlating scores at each time point.

As described herein a "janus kinase inhibitor", "JAK inhibitor" or "JAK kinase inhibitor" is an inhibitor of a member of the janus kinase (JAK) family of kinases. In an embodiment, the JAK inhibitor is a JAK1, JAK2 and/or JAK3 inhibitor. In an embodiment, the JAK inhibitor is an inhibitor of a kinase in the enzyme class EC 2.7.10.2. In an embodiment, the JAK inhibitor is a JAK3 inhibitor. In an embodiment, the JAK inhibitor is a JAK2 inhibitor. In an embodiment, the JAK inhibitor is a JAK1 inhibitor. In an embodiment, the JAK inhibitor is an inhibitor of tyrosine kinase 2 (TyK2). In an embodiment, the JAK inhibitor is a small molecule inhibitor. In an embodiment, the JAK inhibitor is a binding protein. In an embodiment, the binding protein is an antibody. In an embodiment, the JAK inhibitor is an aptamer. In an embodiment, the JAK inhibitor is a polynucleotide. In an embodiment, the JAK inhibitor is selected from: tofacitinib, baractinib, ruxolitinib, decernotinib, R348, WHI-P131, WHI-P 154, JAK3 Inhibitor IV, NSC114792, tyrphostin AG 490, momelotinib, pacritinib, fedratinib, and BMS-911543.

It will be understood by the skilled person that all forms of JAK inhibitors are encompassed, including any tautomeric forms.

Whilst some embodiments may involve use of the parent compound, in other embodiments a salt form is utilised, e.g. a pharmaceutically acceptable salt. Examples of salts include those formed with sulphuric acid (sulfate salt) and citric acid (citrate salt). In a preferred embodiment a citrate salt is used, typically the monocitrate salt.

Whilst in some embodiments, the parent compound is utilised, in other embodiments a derivative of the parent compound may be used, for example a physiological functional derivative. Examples of derivatives include sulphonamides, amides, and carbamates. A prodrug form of JAK inhibitor may be utilised. A prodrug is a compound which, upon administration to the recipient, is capable of being converted into the tofacitinib parent compound described above.

Those skilled in the art of organic chemistry will appreciate that many organic compounds can form complexes with solvents in which they are reacted or from which they are precipitated or crystallized. These complexes are known as "solvates". For example, a complex with water is known as a "hydrate".

It will be understood by the skilled person that many organic compounds can exist in amorphous and crystalline forms. Different crystalline forms of a compound are known as polymorphs. All such forms (e.g. amorphous and crystalline polymorphs) of JAK inhibitors are encompassed.

As described herein, the term "tofacitinib" includes a compound having the formula:

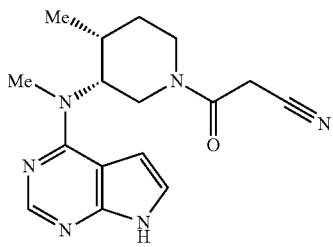 [SMILES: C[C@@H]1CCN(C(=O)CC#N)C[C@@H]1N(C)c1ncnc2[nH]ccc12]

and salts thereof.

Tofacitinib is also known as "tasocitinib", "tofacitinibum" "CP-690550" or "CP690550". Tofacitinib (CAS ID: 540737-29-9) (UNII: O1FF4DIVOD) (PubChem CID: 10174505) is a janus kinase (JAK) inhibitor. It will be understood by the skilled person that all forms of tofacitinib are encompassed, including any tautomeric forms. Whilst some embodiments may involve use of the parent compound, in other embodiments a salt form is utilised, e.g. a pharmaceutically acceptable salt. Examples of salts include those formed with sulphuric acid (sulfate salt) and citric acid (citrate salt). In a preferred embodiment a citrate salt is used, typically the monocitrate salt, referred to for example as tofacitinib citrate, tasocitinib citrate, tofacitinib monocitrate or tasocitinib monocitrate. In one embodiment, tofacitinib citrate is made by combining equimolar amounts of tofacitinib free base and citric acid.

Whilst in some embodiments, the parent compound is utilised, in other embodiments a derivative of the parent compound may be used, for example a physiological functional derivative. Examples of derivatives include sulphonamides, amides, and carbamates. A prodrug form of tofacitinib may be utilised. A prodrug is a compound which, upon administration to the recipient, is capable of being converted into the tofacitinib parent compound described above.

It will be understood by the skilled person that solvates of tofacitinib, as well as solvates of salts and derivatives thereof are encompassed. Solvates of tofacitinib which are suitable for use in medicine are those wherein an associated solvent is pharmaceutically acceptable. For example, a hydrate is an example of a pharmaceutically acceptable solvate. In some embodiments, a solvate is used. In some embodiments, a hydrate is used.

It will be understood by the skilled person that many organic compounds can exist in amorphous and crystalline forms. Different crystalline forms of a compound are known as polymorphs. All such forms (e.g. amorphous and crystalline polymorphs) of tofacitinib are encompassed.

As described herein, "tofacitinib" also known as "tasocitinib", "tofacitinibum" "CP-690550" or "CP690550" is a janus kinase inhibitor (CAS ID: 540737-29-9) (UNII: O1FF4DIVOD) (PubChem CID: 10174505). Tofacitinib is primarily metabolized by the enzymatic hepatic pathway cytochrome P450 (CYP-450) 3A4, with minor metabolism using the CYP2C19 pathway. The term "tofacitinib" is also used in a broad sense to include derivatives thereof. Suitable derivatives include pharmaceutically acceptable salts, pharmaceutically acceptable solvates, pharmaceutically acceptable hydrates, pharmaceutically acceptable sulfates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc. In a preferred embodiment, tofacitinib is tofacitinib citrate also referred to as "tofacitinib monocitrate" or "tasocitinib monocitrate". In an embodiment, tofacitinib citrate is made by combining equimola amounts of tofacitinib and citric acid.

As described herein, "baricitinib" also known as LY 3009104 is a JAK1/JAK2 inhibitor (CAS ID: 1187594-09-7).

As described herein, "ruxolitinib" also known as "INCB 018424" is a JAK1/JAK2/JAK3 inhibitor (CAS ID: 1092939-17-7).

As described herein, "R348" is a JAK/SYK inhibitor (spleen tyrosine kinase).

As described herein, "WHI-P131" also known as "Janex 1" is a JAK3 inhibitor (CAS ID: 202475-60-3).

As described herein, "WHI-P 154" is a JAK3 inhibitor (CAS ID: 211555-04-3).

As described herein, "decernotinib" also known as "VX-509" is a JAK3 inhibitor (CAS ID: 944842-54-0).

As described herein, "JAK3 Inhibitor IV" also known as "ZM 39923 hydrochloride" is a JAK3 inhibitor (CAS ID: 58753-54-1).

As described herein, "JAK3 Inhibitor VIII" also known as "NSC114792" is a JAK3 inhibitor (CAS ID: 17392-79-9).

As described herein, "tyrphostin AG 490" also known as "AG490" is a JAK2 inhibitor (CAS ID: 133550-30-8).

As described herein, "momelotinib" also known as "CYT387" is a JAK1/JAK2 inhibitor (CAS ID: 1056634-68-4).

As described herein, "pacritinib" also known as "SB1518" is a JAK2 inhibitor (CAS ID: 937272-79-2).

As described herein, "fedratinib" also known as "TG101348" is a JAK2 inhibitor (CAS ID: 936091-26-8).

As described herein, "BMS-911543" is a JAK2 inhibitor (CAS ID: 1271022-90-2).

As described herein, "WP-1034" is a JAK inhibitor (CAS ID: 1271022-90-2).

As described herein, "spironolactone" is an aldosterone antagonist and has been used as a potassium-sparing diuretic for over 50 years (CAS ID: 52-01-7). It is structurally a steroid, with basic steroid nuclei with four rings.

As described herein, "finasteride", also referred to as "propecia", is a type II 5α-reductase inhibitor, it acts by inhibiting the activity of 5α-reductase, an enzyme that converts testosterone to dihydrotestosterone (CAS ID: 98319-26-7). It is a synthetic drug for the treatment of benign prostatic hyperplasia and male pattern baldness and can be administered orally.

As described herein, "dutasteride" is a 5-α reductase inhibitor that inhibits conversion of testosterone to dihydrotestosterone (CAS ID: 164656-23-9).

As described herein, "flutamide" is a non-steroidal anti-androgen (CAS ID: 13311-84-7).

As described herein, "cyproterone" is a steroidal antiandrogen (CAS ID: 2098-66-0).

As described herein, "bicalutamide" is a non-steroidal antiandrogen (CAS ID: 90357-06-5).

As described herein, "enzalutamide" is a non-steroidal antiandrogen (CAS ID: 90357-06-5).

As described herein, "nilutamide" is a non-steroidal anti-androgen (CAS ID: 90357-06-5).

As described herein, "drosperidone" is a progestogen (CAS ID: 67392-87-4)

As described herein, "apalutamide" is a non-steroidal antiandrogen (CAS ID: 90357-06-5).

As described herein, "buserilin" is a non-steroidal antiandrogen (CAS ID: 90357-06-5).

As described herein, "saw palmetto" is a non-steroidal antiandrogen (CAS ID: 90357-06-5).

As described herein, "azaleic acid" is a non-steroidal antiandrogen (CAS ID: 90357-06-5).

As described herein, "minoxidil" also known as "2,4-Diamino-6-piperidinopyrimidine 3-oxide" or "2,4-Pyrimidinediamine, 6-(1-piperidinyl)-, 3-oxide" or "2,6-Diamino-4-piperidinopyrimidin-1-oxid" is a piperidinopyrimidine derivative and a potent vasodilator (CAS ID: 38304-91-5). The term "minoxidil" is used in broad sense to include not only "minoxidil" per se but also its pharmaceutically acceptable derivatives thereof.

As described herein, "setipiprant" is a prostaglandin $D_2$ receptor antagonist (CAS ID: 866460-33-5).

As described herein, "fevipiprant" is a prostaglandin D2 receptor antagonist (CAS ID: 872365-14-5).

As described herein, "cyclosporin" also called "cyclosporine" or "ciclosporin" is an immunosuppressant (CAS ID: 59865-13-3).

As described herein, "methotrexate" is an immunosuppressant (CAS ID: 59-05-2).

As described herein, "azathioprine" is an immunosuppressant (CAS ID: 446-86-6).

As described herein, "prednisolone" is a glucocorticoid (CAS ID: 50-24-8).

As described herein, "dexamethasone" is a glucocorticoid (CAS ID: 50-02-2)

As used herein the term "subject" refers to a mammal, particularly a human. In an embodiment the subject, is male. In an embodiment the subject, is female.

As used herein, the terms "treating" or "treatment" of hair loss or hair shedding means: (1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms.

As used herein, the terms "promoting" or "promotion" of hair growth refers to inducing or supporting hair growth. In an embodiment, promoting hair growth increases the number of hair follicles in the anagen hair growth phase. In an embodiment, promoting hair growth comprises increasing the length of the anagen hair growth phase. In an embodiment, promoting hair growth comprises increasing the initiation of the anagen hair growth phase. In an embodiment, promoting hair growth decreases the length of the telogen hair growth phase. In an embodiment, promoting hair growth decreases the length of the catgen hair growth phase. In an embodiment, promoting hair growth decreases the length of the kenogen hair growth phase. In an embodiment, promoting hair growth comprises increasing hair length. In an embodiment, promoting hair growth comprises increasing the diameter of hair fibres. In an embodiment, promoting hair growth comprises increasing the number of hairs in a hair follicle. In an embodiment, promoting hair growth increases the number of frontal scalp terminal hairs. In an embodiment, promoting hair growth comprises promoting scalp hair growth in a subject. In an embodiment, promoting hair growth comprises promoting beard growth in a subject. In an embodiment, promoting hair growth comprises promoting eyebrow growth in a subject. In an embodiment, promoting hair growth comprises promoting eyelash growth in a subject. In an embodiment, promoting hair growth comprises increasing hair length in a subject.

The methods and compositions as described herein are relevant to the treatment of "autoimmune disease". An autoimmune disease is a disease caused by an immune response against a normal component of the body (i.e. where the body mounts an immune response against its own components). In an embodiment, the autoimmune disease is selected from one or more of: rheumatoid arthritis, psoriasis, psoriatic arthritis, vitiligo, sarcoid, atopic dermatitis, ulcerative colitis, lupus erythematosus, lichen planus, Hashimoto's disease, Graves' disease, Crohn's disease, alopecia and alopecia areata.

The methods and compositions as described herein are relevant to the treatment of "hair loss". One particular form of "hair loss" is "hair shedding" described as where hair falls out from skin areas where it is usually present, such as the scalp. Hair shedding can be described as either normal levels of hair shedding or excessive levels of hair shedding. Excessive hair loss or hair shedding may be a consequence of one of the following conditions: alopecia areata, alopecia totalis, alopecia universalis, androgenetic alopecia, telogen effluvium (chronic and acute), anagen effluvium, chemotherapy induced hair loss, male pattern baldness, female pattern baldness, thyroid problems, monilethrix, anaemia, congenital hypotrichosis, hypotrichosis, short anagen syndrome, loose anagen syndrome, drug induced and chemotherapy induced hair loss, cicatricial alopecia, polycystic ovary syndrome, cicatricial alopecia (lichen planopilaris, discoid lupus erythematosus, folliculitis decalvans), tinea capitis, hypotrichosis simplex, congenital hypotrichosis, hypotrichosis, malnutrition, folliculitis decalvans, tufted folliculitis, alopecia planopilaris, frontal fibrosing alopecia, lichen planopilaris and lichen frontal fibrosing. In an embodiment, the condition is male pattern baldness. In an embodiment, the condition is androgenic alopecia. In an embodiment, the condition is telogen effluvium. In an embodiment, the condition is chronic telogen effluvium. In an embodiment, the condition is acute telogen effluvium. In an embodiment, the subject is female. In an embodiment, the subject is male. A subject may be diagnosed by one or more of the above conditions by any method known to a person skilled in the art.

In an embodiment, the alopecia areata is selected from: mild alopecia areata, moderate alopecia areata, severe alopecia areata. In an embodiment, the alopecia areata is treatment resistant alopecia areata.

In an embodiment, treatment resistant alopecia areata is resistant to treatment with cyclosporine.

In an embodiment, the methods and compositions as described herein reduce the relapse of alopecia areata and/or increase the rate of recovery from alopecia areata.

In an embodiment, the methods and compositions as described herein reduce chemotherapy induced hair loss or excessive hair shedding and/or increase the rate of recovery from chemotherapy induced hair loss or excessive hair shedding.

As described herein, "predominantly absorbed through the oral mucosa" indicates that the greatest proportion of a dose or composition enters the blood stream by absorption through the oral mucosa compared to other mucosa. For example, a greater proportion of the dose or composition enters that blood stream through the oral mucosa than through the mucosa of the lower gastrointestinal tract (e.g. intestines and stomach). In an embodiment, about 50% to about 98% of an absorbed dose or composition is absorbed through the oral mucosa. In an embodiment, about 55% to about 95% of an absorbed dose or composition is absorbed through the oral mucosa. In an embodiment, about 58% to about 90% of an absorbed dose or composition is absorbed through the oral mucosa. In an embodiment, about 60% to about 85% of an absorbed dose or composition is absorbed through the oral mucosa. In an embodiment, about 65% to about 80% of an absorbed dose or composition is absorbed through the oral mucosa. In an embodiment, about 70% to about 75% of an absorbed dose or composition is absorbed through the oral mucosa.

A dose or composition that is predominantly absorbed through the oral mucosa can be orodispersible. As used described herein "orodispersible" refers to a dose or dosage form that dissolves, disintegrates and/or disperses in the mouth/oral cavity allowing for absorption in the mouth/oral cavity. Such dosage forms may also be referred to as "mouth dissolving" dosage forms.

As described herein, "predominantly absorbed through the sublingual mucosa" indicates that the greatest proportion of a dose or composition enters the blood stream by absorption through the sublingual mucosa compared to other mucosa. In an embodiment, about 50% to about 98% of an absorbed dose or composition is absorbed through the sublingual mucosa. In an embodiment, about 55% to about 95% of an absorbed dose or composition is absorbed through the sublingual mucosa. In an embodiment, about 58% to about 90% of an absorbed dose or composition is absorbed through the sublingual mucosa. In an embodiment, about 60% to about 85% of an absorbed dose or composition is absorbed through the sublingual mucosa. In an embodiment, about 65% to about 80% of an absorbed dose or composition is absorbed through the sublingual mucosa. In an embodiment, about 70% to about 75% of an absorbed dose or composition is absorbed through the sublingual mucosa. In an embodiment, a dose or composition that is predominantly absorbed through the sublingual mucosa can be placed under the tongue and dissolved under the tongue. The dose or composition may comprise an adhesive agent that aids association with the sublingual mucosa.

As described herein, "orally administered" refers to a dose or composition that is administered orally and predominantly absorbed in the lower gastrointestinal tract e.g. the intestines or stomach (orally administered drugs are not predominantly absorbed through the oral mucosa or sublingual mucosa). Orally administered drugs are e.g. pills or tablets formulated for oral administration (are swallowed) and are absorbed in the intestines/lower gastrointestinal tract/gastrointestinally. Oral bioavailability (F %) is the fraction of an orally administered drug that reaches the systemic circulation unchanged. The oral bioavailability of a drug can be reduced by incomplete absorption in the gastrointestinal tract or degradation into metabolites during first-pass metabolism in the liver.

As described herein, the "oral mucosa" refers to the mucous membrane lining the inside the oral cavity, which includes the sublingual mucosa, the buccal mucosa, the gingival mucosa, the palatal mucosa, the labial mucosa and/or the alveolar mucosa. A person skilled in the art would appreciate that the methods and compositions as described herein relate to a dose or composition comprising a JAK inhibitor that can enter the blood stream by crossing the oral mucosa. In a preferred embodiment, the JAK inhibitor is tofacitinib.

As used herein, the term "sublingual" or "sublingually" refers to the pharmacological route of administration wherein a desired substance is transported across the membrane by e.g. diffusion, active transport and/or is endocytosed into the circulatory system through tissues under the tongue (the sublingual mucosa). The sublingual mucosa can be divided into two layers the epithelium and the connective tissue which comprises a large capillary structure. The sublingual epithelium is relatively thin compared to other oral epitheliums like the buccal epithelium which is thicker. It comprises higher amounts of polar lipids (e.g. phospholipids, cholesterol esters and glycocerimides) than e.g. palate and gingival mucosa. The sublingual mucosa has a different permeability profile to other regions of the oral mucosa.

As used herein, the "elimination half-life" refers to the time required for the amount of drug in the body to decrease by half.

In one embodiment, the sublingual compositions comprising a JAK inhibitor as described herein have a higher elimination half-life than an orally administered composition comprising the same concentration of a JAK inhibitor. In one embodiment, the sublingual compositions comprising tofacitinib as described herein have a higher elimination half-life than an orally administered composition comprising the same concentration of tofacitinib. In one embodiment, the elimination half-life of the sublingual composition is about 1 to 9 hours higher than the orally administered dose. In one embodiment, the elimination half-life of the sublingual composition is about 1 to 8 hours higher than the orally administered composition. In one embodiment, the elimination half-life of the sublingual composition is about 1 to 7 hours higher than the orally administered composition. In one embodiment, the elimination half-life of the sublingual composition is about 1 to 6 hours higher than the orally administered composition. In one embodiment, the elimination half-life of the sublingual composition is about 1 to 5 hours higher than the orally administered composition. In one embodiment, the elimination half-life of the sublingual composition is about 1 to 4 hours higher than the orally administered composition. In one embodiment, the elimination half-life of the sublingual composition is about 1 to 3 hours higher than the orally administered composition. In one embodiment, the elimination half-life of the sublingual composition is at least 1 hour higher than the orally administered composition. In one embodiment, the elimination half-life of the sublingual composition is at least 2 hours higher than the orally administered composition. In one embodiment, the elimination half-life of the sublingual composition is at least 3 hours higher than the orally administered composition. In one embodiment, the elimination half-life of the sublingual composition is at least 4 hours higher than the orally administered composition. In one embodiment, the elimination half-life of the sublingual composition is at least 5 hours higher than the orally administered composition. In one embodiment, the elimination half-life of the sublingual composition is at least 6 hours higher than the orally administered composition. In one embodiment, the elimination half-life of the sublingual composition is at least 7 hours higher than the orally administered composition. In one embodiment, the elimination half-life of the sublingual composition is at least 8 hours higher than the orally administered composition. In one embodiment, the elimination half-life of the sublingual composition is at least 9 hours higher than the orally administered composition. In one embodiment, the elimination half-life of the sublingual composition is at least 10 hours higher than the orally administered composition.

In one example, the sublingual composition has an elimination half-life of about 3 to 12 hours. In one example, the sublingual composition has an elimination half-life of about 3 to 11 hours. In one example, the sublingual composition has an elimination half-life of about 4 to 11 hours. In one example, the sublingual composition has an elimination half-life of about 5 to 11 hours. In one example, the sublingual composition has an elimination half-life of about 6 to 11 hours. In one example, the sublingual composition has an elimination half-life of about 7 to 11 hours. In one example, the sublingual composition has an elimination half-life of about 8 to 11 hours. In one example, the sublingual composition has an elimination half-life of about 9 to 11 hours. In one example, the sublingual composition has an elimination half-life of about 10 to 11 hours.

A dose or composition comprising a JAK inhibitor as described herein is formulated for absorption across the oral mucosa. Absorption across the oral mucosa may include absorption across one or more of the sublingual mucosa, the buccal mucosa, the labial mucosa, the gingival mucosa, the palatal mucosa, and/or the alveolar mucosa. In a preferred embodiment, the dose or the composition comprising a JAK inhibitor is formulated for absorption across the sublingual mucosa.

A person skilled in the art will appreciate that the dose of tofacitinib or composition comprising tofacitinib may be formulated in any form that allows tofacitinib to cross the oral mucous membrane, such forms include, but are not limited to a; strip, wafer, film, troche, lipid matrix tablet, tablet (including a mini-tablet), capsule, pill, granule, pellet, powder, drop, spray and lozenge. In an embodiment, the dose is formulated as a semi-solid dosage form. In an embodiment, the spray is a powder. In an embodiment, the powder is packaged in a sachet. In an embodiment the dose of tofacitinib or composition comprising tofacitinib is formulated as a strip, wafer, pellet or film which disintegrates when placed under the tongue. In an embodiment the dose of tofacitinib or composition comprising tofacitinib is formulated as an "orodispersible strip", "orodispersible wafer" or an "orodispersible film".

In an embodiment, the strip, wafer or film disperses/disintegrates sublingually. In an embodiment, the film may be selected from a flash release, mucoadhesive melt-away or a mucoadhesive sustained release film for example as described in Nagaraju et al. (2013). In an embodiment, the dose of tofacitinib or composition comprising tofacitinib is formulated in a spray. In an embodiment, the spray can be applied to the buccal mucosa and/or the sublingual mucosa. In an embodiment, the dose of tofacitinib or composition comprising tofacitinib is not a nanoparticle composition.

The dose or composition comprising a JAK inhibitor may be formulated for rapid disintegration to ensure the JAK inhibitor is absorbed through the oral mucosa or the sublingual mucosa. In an embodiment, such doses or compositions will be formulated to disintegrate in the presence of saliva and/or water. In an embodiment, such formulations may comprise a disintegration agent which aids disintegration of the dose or composition in the presence of saliva and/or the presence of water.

In an embodiment, the dose or composition comprising a JAK inhibitor is stable at between about 0° C. to about 40° C.

In an embodiment, the dose or composition comprising a JAK inhibitor is a sublingual composition. In an embodiment, the sublingual composition is a sublingual strip.

As used herein the "disintegrating agent", "disintegration agent" or "disintegrant/s" refers to an agent added to the dose or composition that facilitates disintegration/dispersion of the formulation in the oral cavity or sublingually and includes superdisintegrating agents and effervescent agents. Disintegrants may act by water wicking, capillary action, swelling, deformation, repulsion (e.g. release of gasses), and heat of wetting.

Examples of disintegrating agents can be found in Gad et al. (2008) and Rowe et al. (2009) and include for example, but are not limited to, starch, modified starches, crosslinked starches, crosslinked alginic acid, modified cellulose and cross-linked povidone, microcrystalline cellulose, sodium starch glycollate (Primojel, Explotab), cassia fistula gum, crospovidone, croscarmellose sodium, alginic acid, sodium alginate, starch USP, starch 1500, avicel, solka floc, alginic acid, sodium alginate, polyplasdone, amberlite, methyl cellulose, AC-Di-Sol, carbon dioxide, lepidum sativum, locust bean gum, nymce ZSX, primellose, solutab, vivasol crospovidone, crospovidone M, kollidon, polyplasdone, plantagoovata husk, Plantago ovate mucilage, cetric acid, satialgine, soy polysaccharides, sodium bicarbonate, sodium starch glycolate, treated agar, emcosoy, and calcium silicate. Disintegrating agents that are particularly suitable for use in strips and films are described in Nagaraju et al. (2013).

In an embodiment, the disintegrating agent swells at least 2 fold in under 10 seconds, or at least 3 fold in under 10 seconds, or at least 4 fold in under 10 seconds, or at least 5 fold in under 10 seconds, or at least 6 fold in under 10 seconds, or at least 7 fold in under 10 seconds, or at least 8 fold in under 10 seconds. In an embodiment, the disintegrating agent swells at least 2 fold in under 30 seconds, or at least 3 fold in under 30 seconds, or at least 4 fold in under 30 seconds, or at least 5 fold in under 30 seconds, or at least 6 fold in under 30 seconds, or at least 7 fold in under 30 seconds, or at least 8 fold in under 30 seconds, or at least 9 fold in under 30 seconds, or at least 10 fold in under 30 seconds, or at least 11 fold in under 30 seconds, or at least 12 fold in under 30 seconds.

In an embodiment, the dose or composition comprising a JAK inhibitor is formulated so that an oral disintegrating enzyme facilitates disintegration in the oral cavity. In an embodiment, the oral disintegrating enzyme is amylase (which acts upon starch), protease (which acts upon gelatin), cellulase (which acts upon cellulose and/or its derivatives) and/or invertase (which acts upon sucrose).

In an embodiment, the dose or composition comprising a JAK inhibitor is formulated to disintegrate/disperse in under about 2 minutes, or in under about 1 minute, or in under about 50 seconds, or in under about 40 seconds, or in under about 30 seconds, or in under about 20 seconds, or in under about 15 seconds, or in under about 10 seconds of being placed in the mouth.

In an embodiment, the dose of composition comprising a JAK inhibitor is formulated to disintegrate/disperse in under about 2 minutes, or in under about 1 minute, or in under about 50 seconds, or in under about 40 seconds, or in under about 30 seconds, or in under about 25 seconds, or in under about 20 seconds, or in under about 18 seconds, or in under about 15 seconds, or in under about 12 seconds, or in under about 10 seconds, or in under about 5 seconds of being placed under the tongue. In an embodiment, the dose or composition comprising a JAK inhibitor is formulated to disintegrate/disperse in under about 30 seconds of being placed under the tongue.

The disintegration times of oral and sublingual doses as described herein can be assessed as described for example in Narang et al (2001) and USP/NP. Physical Tests: Disintegration (701).

In an embodiment, the dose or composition comprising a JAK inhibitor may comprise an adhesive agent which aids adherence of the dose or composition to the sublingual mucosa. In an embodiment, the adhesive agent is a bioadhesion. In an embodiment, the adhesive agent is a mucoadhesion. A bioadhesion or mucoadhesion can aid in keeping the dose or composition comprising a JAK inhibitor in intimate contact with the sublingual mucosa, and/or to increase the time in contact with the sublingual mucosa. The presence of an adhesive agent can also prevent inadvertent swallowing of the dose.

In an embodiment, the dose or composition comprising a JAK inhibitor may comprise a taste modifying agent to improve the taste of the dose or composition for the subject. Taste modifying agents include sweeteners and flavouring agents. Examples of taste modifying agents can be found in Gad et al. (2008), Rowe et al. (2009) and Nagaraju et al. (2013) and include, for example mannitol, aspartame, sucrose, dextrose, fructose, glucose, maltose, neotame, alitame, saccharin and sorbitol.

A person skilled in the art will appreciate that such dosage forms or compositions may be prepared by any method known to a person skilled in the art and can include, for example: freeze-drying or lyophilisation, sublimation, spray drying, moulding, direct compression, melt granulation, mass extrusion, effervescent method, 3D printing and ink-jet technology (for application of tofacitinib to strips, wafers and films). Examples of such methods can be found in Dey and Maiti (2010); Jamróz et al (2017); and Singh et al (2012).

Films as described herein may also be produced by any method known to a person skilled in the art, and for example, by the methods described in Nagaraju et al. (2013), Amin et al. (2015) and Irfan et al. (2016) which include casting and drying (solvent casting or semi-solid casting), extrusion (hot-melt extrusion or solid dispersion extrusion), rolling method and spray technique.

In one example, producing films by hot-melt extrusion comprises: mixing of hydrophilic acid insoluble polymers, addition of a JAK inhibitor and plasticizer, extrusion, drying and cutting of the extrusion into films.

In one example, producing films by solvent casting comprises: preparation of a solvent suspension comprising a JAK inhibitor, casting of a solvent suspension, drying of the solvent suspension, film stripping and film packaging.

In one example, producing films by solid dispersion extrusion comprises: mixing of a JAK inhibitor with a suitable solvent, adding the mixture of a JAK inhibitor and solvent to a melted polymer along with immiscible components and cutting of the solid dispersion into a film.

In one example, producing films by the rolling method comprises: preparation of a suspension comprising a JAK inhibitor and polymer in water or alcohol, subjecting the suspension to rollers, evaporation of solvent and cutting into film.

Films as described herein may comprise one or more of the following: a film forming agent, a plasticizer, taste modifying agent, surfactant, thickener and/or stabilizer, a saliva stimulating agent, an adhesive agent and a colouring agent.

"Film forming agent" refers to a polymer capable of forming a film. In an embodiment, the film forming agent may be selected from: hydroxypropylmethyl cellulose (HPMC), hydroxypropyl cellulose (HPC), pullulan, carboxymethyl cellulose (CMC), pectin, starch, polyvinyl acetate (PVA), and sodium alginate.

"Plasticizer" refers to an agent which improves the flexibility and/or decreases the brittleness of a film. In an embodiment, the plasticizer may be selected from: glycerine, sorbitol propylene glycerol, glycerol, caster oil, triacetin, trithyl citrate, acetyl triethyl citrate and other citrate esters.

In an embodiment, the dose or composition comprises a JAK inhibitor in the range from about 0.1 mg to 50 mg, or from about 0.1 mg to 40 mg, or from about 0.1 mg to 30 mg, or from about 0.1 mg to about 20 mg, or from about 0.2 to about 20 mg, or from about 0.5 mg to 20 mg, or from about 0.5 mg to 18 mg, or from about 0.5 mg to 15 mg, or from about 0.5 mg to 12.5 mg, or from about 0.5 mg to 10 mg, or from about 0.5 mg to 8 mg, or from about 1 mg to 6 mg, or from about 1 mg to 5 mg, or from about 1 mg to 4 mg, or from about 1 mg to 3 mg, or from about 1 mg to 2 mg, or is about 10 mg, or is about 8 mg, or is about 7.5 mg, or is about 5 mg, or is about 4 mg, or is about 3 mg, or is about 2.5 mg, or is about 2 mg, or is about 1 mg, or is about 0.5 mg, or is about 0.1 mg.

In an embodiment, the dose or composition comprises a JAK inhibitor in the range from about 0.1 mg to about 50 mg. In an embodiment, the dose or composition comprises a JAK inhibitor in the range from about 0.1 mg to about 20 mg. In an embodiment, the dose or composition comprises a JAK inhibitor in the range from about 0.2 to about 20 mg. In an embodiment, the dose or composition comprises a JAK inhibitor in the range from about 0.5 mg to 20 mg. In an embodiment, the dose or composition comprises a JAK inhibitor in the range of from about 0.5 mg to 18 mg. In an embodiment, the dose or composition comprises a JAK inhibitor in the range of from about 0.5 mg to 15 mg. In an embodiment, the dose or composition comprises a JAK inhibitor in the range of from about 0.5 mg to 12.5 mg. In an embodiment, the dose or composition comprises a JAK inhibitor in the range of from about 0.5 mg to 10 mg. In an embodiment, the dose or composition comprises a JAK inhibitor in the range of from about 0.5 mg to 10 mg. In an embodiment, the dose or composition comprises a JAK inhibitor in the range of from about 0.5 mg to 8 mg. In an embodiment, the dose or composition comprises a JAK inhibitor in the range of from about 1 mg to 6 mg. In an embodiment, the dose or composition comprises a JAK inhibitor in the range of from about 1 mg to 5 mg. In an embodiment, the dose or composition comprises a JAK inhibitor in the range of from about 1 mg to 4 mg. In an embodiment, the dose or composition comprises a JAK inhibitor in the range of from about 1 mg to 3 mg. In an embodiment, the dose or composition comprises a JAK inhibitor in the range of from about 1 mg to 2 mg. In an embodiment, the dose or composition comprises a JAK inhibitor at a concentration of about 10 mg. In an embodiment, the dose or composition comprises a JAK inhibitor at a concentration of about 8 mg. In an embodiment, the dose or composition comprises a JAK inhibitor at a concentration of about 7.5 mg. In an embodiment, the dose or composition comprises a JAK inhibitor at a concentration of about 6 mg. In an embodiment, the dose or composition comprises a JAK inhibitor at a concentration of about 5.5 mg. In an embodiment, the dose or composition comprises a JAK inhibitor at a concentration of about 5 mg. In an embodiment, the dose or composition comprises a JAK inhibitor at a concentration of about 4.5 mg. In an embodiment, the dose or composition comprises a JAK inhibitor at a concentration of about 4 mg. In an embodiment, the dose or composition comprises a JAK inhibitor at a concentration of about 3 mg. In an embodiment, the dose or composition comprises a JAK inhibitor at a concentration of about 2.5 mg. In an embodiment, the dose or composition comprises a JAK inhibitor at a concentration of about 2 mg. In an embodiment, the dose or composition comprises a JAK inhibitor at a concentration of about 1 mg. In an embodiment, the dose or composition comprises a JAK inhibitor at a concentration of about 0.5 mg. In an embodiment, the dose or composition comprises a JAK inhibitor at a concentration of about 0.1 mg.

In an embodiment, the dose or composition comprises tofacitinib in the range of from about 0.1 mg to 50 mg, or from about 0.1 mg to 40 mg, or from about 0.1 mg to 30 mg, or from about 0.1 mg to 20 mg, or from about 0.1 mg to 18 mg, or from about 0.1 mg to 15 mg, or from about 0.2 mg to 12.5 mg, or from about 0.2 mg to 10 mg, or from about 0.5 mg to 8 mg, or from about 1 mg to 6 mg, or from about 1 mg to 5 mg, or from about 1 mg to 4 mg, or from about 1 mg to 3 mg, or from about 1 mg to 2 mg, or is about 10 mg, or is about 8 mg, or is about 7.5 mg, or is about 5 mg, or is about 4 mg, or is about 3 mg, or is about 2.5 mg, or is about 2 mg, or is about 1 mg, or is about 0.5 mg, or is about 0.1 mg daily.

In an embodiment, the dose or composition comprises tofacitinib in the range of from about 0.1 mg to 50 mg. In an embodiment, the dose or composition comprises tofacitinib in the range of from about 0.1 mg to 20 mg. In an embodiment, the dose or composition comprises tofacitinib in the range of from about 0.1 mg to 18 mg. In an embodiment, the dose or composition comprises tofacitinib in the range of from about 0.1 mg to 15 mg. In an embodiment, the dose or composition comprises tofacitinib in the range of from about 0.2 mg to 12.5 mg. In an embodiment, the dose or composition comprises tofacitinib in the range of from about 0.2 mg to 10 mg. In an embodiment, the dose or composition comprises tofacitinib in the range of from about 0.5 mg to 8 mg. In an embodiment, the dose or composition comprises tofacitinib in the range of from about 1 mg to 6 mg. In an embodiment, the dose or composition comprises tofacitinib in the range of from about 1 mg to 5 mg. In an embodiment, the dose or composition comprises tofacitinib in the range of from about 1 mg to 4 mg. In an embodiment, the dose or composition comprises tofacitinib in the range of from about 1 mg to 3 mg. In an embodiment, the dose or composition comprises tofacitinib in the range of from about 1 mg to 2 mg. In an embodiment, the dose or composition comprises tofacitinib at a concentration of about 10 mg. In an embodiment, the dose or composition comprises tofacitinib at a concentration of about 8 mg. In an embodiment, the dose or composition comprises tofacitinib at a concentration of about 7.5 mg. In an embodiment, the dose or composition comprises tofacitinib at a concentration of about 6 mg. In an embodiment, the dose or composition comprises tofacitinib at a concentration of about 5.5 mg. In an embodiment, the dose or composition comprises tofacitinib at a concentration of about 5 mg. In an embodiment, the dose or composition comprises tofacitinib at a concentration of about 4.5 mg. In an embodiment, the dose or composition comprises tofacitinib at a concentration of about 4 mg. In an embodiment, the dose or composition comprises tofacitinib at a concentration of about 3 mg. In an embodiment, the dose or composition comprises tofacitinib at a concentration of about 2.5 mg. In an embodiment, the dose or composition comprises tofacitinib at a concentration of about 2 mg. In an embodiment, the dose or composition comprises tofacitinib at a concentration of about 1 mg. In an embodiment, the dose or composition comprises tofacitinib at a concentration of about 0.5 mg. In an embodiment, the dose or composition comprises tofacitinib at a concentration of about 0.1 mg.

In an embodiment, the dose or composition comprising a JAK inhibitor is administered weekly, bi-weekly, every three days, every second day, one or more times a day. In an embodiment, the dose or composition comprising a JAK inhibitor is administered one or more times a day. In an embodiment, the dose or composition comprising a JAK inhibitor is administered daily.

In an embodiment, the dose of a JAK inhibitor administered to a subject may be increased over time.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

This application claims priority from U.S. Provisional Application No. 62/811,353 entitled "Treatment of Autoimmune Disease" filed on 27 Feb. 2020, the entire contents of that application are hereby incorporated by reference.

All publications discussed and/or referenced herein are incorporates in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The steps, features, integers, compositions and/or compounds disclosed herein or indicated in the specification of this application individually or collectively, and any and all combinations of two or more of said steps or features.

EXAMPLES

Example 1: Orally Administered and Sublingual Tofacitinib for Chronic, Refractory, Moderate to Severe Alopecia Areata Introduction Alopecia areata (AA) is an autoimmune disorder of terminal anagen hair follicles that may produce one or more circular patches of hair loss, complete scalp baldness (alopecia totalis—AT) or universal hair loss (alopecia universalis—AU). AA is the most common autoimmune disease in man. The lifetime risk is estimated to be 2.1% and AA principally affects people aged between 20-40 years. AA has a genetic etiology and cryptogenic environmental trigger. The pathogenesis includes immune dysregulation, loss of hair follicle immune privilege, autoimmunity, hair breakage, hair cycle dysregulation and disturbance of hair pigmentation. There may be associated nail changes.

The clinical severity, disease trajectory and natural history are heterogeneous and variable. In approximately 40% of affected individuals, the hair loss appears as a single circular patch that resolves spontaneously within six months; a further 27% of affected individuals develop additional patches progressively over a few weeks to months, but still achieve a durable remission within 12 months; while, the remaining 33% of individuals have continued disease at 12 months.

Persistent disease at 12 months predicts a chronic relapsing and remitting course with a 45% risk of ultimately developing AT or AU. Significant psychological sequelae are recognized associations. Effective treatment of chronic AA remains challenging—there is no consensus agreement on use of systemic treatments such as prednisolone, azathioprine, ciclosporin and methotrexate and these options only infrequently produce a satisfactory, durable response and can be associated with undesirable side effects.

This study demonstrates the use of tofacitinib in a clinical setting for the treatment of chronic (defined as disease duration >12 months), moderate to severe AA in 127 patients whose hair loss was refractory to systemic therapy. It is also reported that sublingual tofacitinib treatment produces a response comparable to orally administered tofacitinib in the absence of other components which reduce hepatic metabolism.

Subjects

Patients who received tofacitinib treatment (oral administration or sublingual administration) for a minimum 3 months were included in this study.

Patients' clinical and demographic data were collected. The patients all underwent pre-screening laboratory tests that included: full blood count, biochemistry profile, liver function tests (LFTs), lipid profile, thyroid function tests, HIV, EBV, hepatitis serology, QuantiFERON-TB Gold (Cellestis Limited, Melbourne, Australia), and vitamin D. Additional safety monitoring blood tests including full blood count, biochemistry profile, LFTs and lipid profile were performed at 6-12 weekly intervals.

Patients were treated for up to 18 months with tofacitinib either as monotherapy, or in combination with intralesional and/or systemic therapies. Treatment was titrated according to response and tolerability.

Forty-two (37%) males and 85 (67%) females were included in the analysis. The mean age was 34 years (range 11-68). Twenty-four (19%) were paediatric patients. Sixteen (12.6%) had an autoimmune disease, the majority of which was thyroid disease, or vitiligo. Forty-five had a personal history of atopy. A positive family history of an autoimmune disorder was present in 39 (31%). Ninety (70.8%) had patchy disease, while 35 (26.5%) had AT/AU. Two (1.8%) had exclusive beard AA. The average age of onset of disease was 24 years (range 1-63) and the average duration of disease at baseline was 9.8 years (range 1-40). Duration of disease was determined as starting from the onset of their first AA episode.

In AA, AT and AU, a partial response may not be clinically significant and may be detrimental to patient satisfaction. The ultimate goal of therapy is complete or near complete response/remission, where the patient can readily conceal any residual hair loss. The Severity of Alopecia Tool (SALT) is an ideal means of monitoring incremental or partial responses to therapy but is impossible to estimate retrospectively from photographs (Olsen et al 2004; and Olsen et al 2016). To score clinically meaningful hair regrowth in a retrospective clinical context, a 7-point assessment scale was devised that assigns a simple numerical value to reflect a global impression of treatment response compared to a pre-determined baseline. This was adapted from the classification of severity of AA, first published by Olsen et al (1992) and (1997) and which was formalized by the National Alopecia Areata Foundation Guidelines Committee (Olsen et al 1999), and revised 2004 (Olsen et al 2004). A +3 pertains to a complete response (SALT 0) and −3 represents complete hair loss (SALT 100). This is a dynamic scoring system which is easy to use in a real-world setting and is also easily understood by patients.

TABLE 1

The 7-point assessment scale
Table 1: The 7-point assessment scale

| Score | Scalp Hair Loss Percentage | Clinical Definition |
| --- | --- | --- |
| −3 | 100% hair loss (SALT 100) | Complete hair loss |
| −2 | 75-99% hair loss | Extensive hair loss |
| −1 | 50-74% hair loss | Some hair loss |
| 0 | No change from baseline | No change |
| +1 | 25-49% hair loss | Some hair growth |
| +2 | 1-24% hair loss | Extensive hair growth |
| +3 | No hair loss (SALT 0) | Complete response |

Review of standardized serial photographs (performed as part of routine care) were conducted independently by three individuals to attribute a score on the 7-point assessment scale at three monthly intervals, relative to baseline (pre-first tofacitinib prescription).

Outcome Measures

The primary endpoint was the percentage of patients who achieved +3 (complete response (CR)) at each time point. The secondary endpoints were the mean and median scores and the percentage of patients who achieved a +1 or +2 response at each time point. Early responders—patients who achieved a >+1 score within 3 months of commencing treatment. Late responders—patients who did not achieve a >+1 score until at least 6 months of treatment. Further endpoints of interest were: Prolonged disease duration—patients who had current disease duration >10 years. This was defined based on the patient's report of the first instance of AA. Relapse—at least one grade deterioration in score from the last score. Treatment Failure: Primary failures were patients who failed to achieve a +1 outcome. Secondary failures were patients who achieved >+1 regrowth but then had sustained, at least one grade deterioration from baseline score, for at least 6 months. Patients who withdrew from treatment were considered non-responders. Tofacitinib monotherapy—patients who were not taking any other immunosuppressant medications when they started tofacitinib.

Results

One-hundred and twenty-seven patients were treated for >3 months and were included in the analysis. Fourteen patients ceased treatment and were considered non-responders.

TABLE 2

Baseline patient characteristics
Table 2: Baseline characteristics of our patients Gender:

Male - n = 42 (37%)
Female - n = 85 (67%)
Age: Median 34 years (Range 11-68)

18 years and under - 24 (19%)
19 to 35 years - 47 (37%)
36 to 45 years - 24 (19%)
46 to 59 years - 23 (18%)
60 years and over - 9 (7%)
A personal history of another autoimmune disease - 16 patients (12.6%)

Thyroid disease - 10
Vitiligo - 4
Coeliac disease and Inflammatory bowel disease - 4
Personal history of atopy - 45 patients (35%)

Atopic dermatitis - 39
Asthma - 19
A family history of autoimmune disorders - 39 patients (31%)
Type of AA at baseline:

Patchy AA - 51 (40%)
Ophiasis &/or Sisaihpo pattern AA - 39 (30.7%)
AT/AU - 35 (27.5%)
Beard only - 2 (1.8%)
Family history of AA: 26 of 88 patients (29.5%)
Average age of onset of AA was 24 years (range 1-63)
Average duration of disease at baseline was 9.8 years (range 1-40)
Area affected by AA:

Scalp - 123 (96.8%)
Eyelashes - 44 (34.6%)
Eyebrows - 59 (46.4%)
Beard - 29 (69% of males)
Nails - 22 (17.3%)

Tofacitinib Dose

Tofacitinib is commercially available in Australia in a 5 mg dose tablet. Tofacitinib undergoes extensive first pass metabolism in the liver by the CYP3A4 enzyme. CYP3A4 is a member of the cytochrome P450 superfamily of enzymes. The cytochrome P450 proteins are monooxygenases that catalyze many reactions involved in drug metabolism and synthesis of cholesterol, steroids, and other lipids components. Agents such as clarithromycin, cimetidine and grapefruit seed extract are strong inhibitors of CYP3A4 and co-administration with tofacitinib leads to reduced metabolism and increased serum and tissue levels of tofacitinib. Sublingual dosing bypasses the liver and produces higher serum levels of tofacitinib and higher tissue levels of tofacitinib in the hair follicles.

Orally administered doses: Orally administered tofacitinib doses were compounded extemporaneously. The starting dose was determined by the attending physician, taking into consideration the patient's age, weight, extent of hair loss, previous treatment responses and complications, and patient preferences.

The orally administered doses were compounded with either cimetidine 200 mg daily, clarithromycin 250 mg daily or grapefruit seed extract 200 mg in a single capsule to reduce hepatic metabolism and to increase the serum levels.

In the pediatric group the mean baseline dose was 3 mg daily (1-5 mg), and mean overall treatment dose was 4.7 mg (1-12.5 mg). In the adult group the mean baseline dose was 4.4 mg daily (1-10 mg), and mean overall treatment dose was 5.6 mg (1-20 mg). The maximum treatment dose was 20 mg daily, prescribed for one adult patient. Dosage was titrated in a non-standardized manner by the attending physician according to patient tolerability and response.

Sublingual doses: A sublingual tofacitinib min-tablet was prepared comprising Tofacitinib citrate (Astral Scientific BIOTFC001), PCCA Polyglycol Troche Base; PCCA, #30-1013) and Silica Gel PPTD Micronized (PCCA #30-1009). To prepare 1725 5 mg doses of sublingual tofacitinib 8.625 g/ml of tofacitinib citrate was combined with 1.725 g/ml silica gel and 162.84 g/ml troche base using the following procedure. One side of the min-tab mold was covered with Lab Film-Parafilm M™. In an appropriate size beaker, PCCA Polyglycol Troche was melted at 50° C. Using a mortar and pestle, tofacitinib was titrated with silica gel together to a fine powder. The powder was sifted into a melted base while stirring. A strainer was used to reduce the particle size. The heat was discontinued and stirred until suspended. Using an appropriate size syringe, the melted mixture was distributed into Tablet Triturate 200 mg mold and allowed to congeal at room temperature. The final product was protected from sunlight and stored in an airtight container. The beyond use for troches prepared using the above protocol is estimated to be 180 days.

The starting dose was determined by the attending physician, taking into consideration the patient's age, weight, extent of hair loss, previous treatment responses and complications, and patient preferences. The mean dose of tofacitinib was 6 mg daily (range 1-20). In the paediatric group the mean starting dose was 3 mg daily (1-5 mg), and mean overall treatment dose was 5 mg (1-12.5 mg). In the adult group the mean starting dose was 4.5 mg daily (1-10 mg), and mean overall treatment dose was 6 mg (1-20 mg). The maximum treatment dose was 20 mg daily, prescribed for one adult patient. Dosage was titrated in a non-standardized manner by the attending physician according to patient tolerability and response.

The mean dose of sublingual tofacitinib during the study period was 4.64 mg daily (range 1-20 mg). The mean dose of orally administered tofacitinib during the study period was 5.22 mg daily (range 2-12.5 mg).

Concomitant Treatments

For patients who were thought to be at risk of relapse with cessation of their current systemic therapy, tofacitinib was introduced alongside the existing therapies which were then tapered off. Seventy-one patients (56%) were on immunosuppressive co-therapy when tofacitinib was commenced. Sixty-six of these patients (93%) were receiving prednisolone at a mean maximum dose of 9 mg (range 1.25-25). One patient was taking methotrexate, 3 patients were taking azathioprine and 17 patients were taking ciclosporin at baseline with or without prednisolone. Thirty-three of these patients (46%) successfully discontinued all other immunosuppressive treatment at some point after starting tofacitinib.

Oral or intralesional corticosteroids were introduced to 82 patients who were either slow to respond, partial responders, or who relapsed on tofacitinib therapy. Twenty-four of these patients (29%) were treated with oral prednisolone at a mean maximum dose of 16 mg (range 5-25) for a mean period of 5 months (range 1-13). Seventy-four of these patients (58%) had intralesional triamcinolone acetonide (mean concentration 5 mg/ml, range 2.5-20 mg/ml; mean quantity 2 ml, range 0.4-5 ml) administered a mean of 4.5 times (range 1-11). Tofacitinib efficacy and time to response Tofacitinib Efficacy and Time to Response Primary endpoint (table 3 and 4): After 3 months, 12% of patients achieved CR. At 12 months, 40% had achieved CR. At 18 months 80% had achieved CR. Twenty-four patients remain in CR (complete response) after six months of continued treatment, whilst another nine have remained in CR for >12 months. Dose reduction has commenced in 3 patients.

Figure 2:
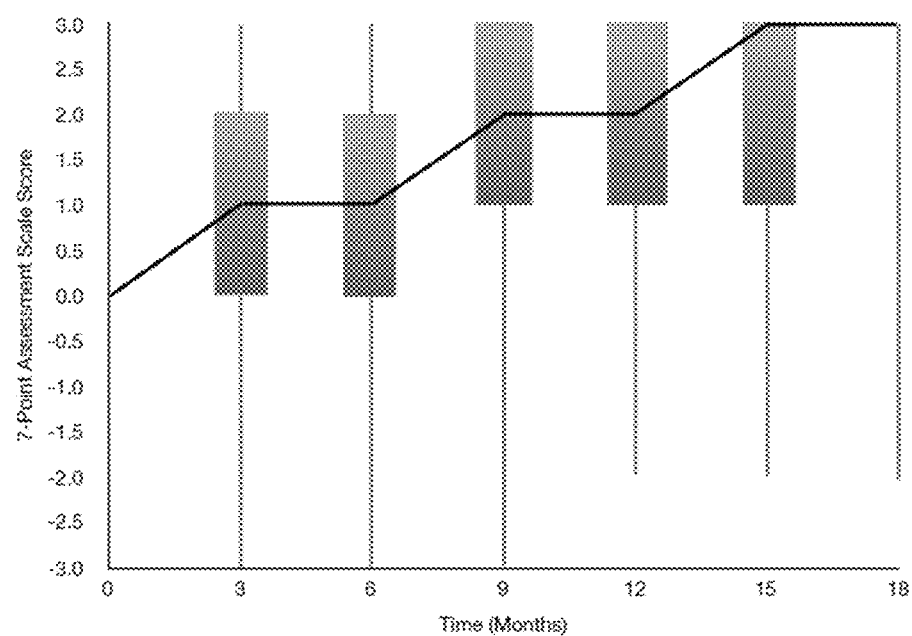
FIG. 2: Shows box and whisker plot of all scores of all patients. The black continuous line highlights the median scores at each time point. The mean score at 3 months was 0.8, at 6 months was 1.1, at 9 months was 1.1, at 12 months was 1.6, at 15 months was 1.9, and at 18 months was 2.4. The boxes represent the inter-quartile range (IQR). The whiskers denote the upper and lower absolute scores.

Secondary endpoints (FIG. 2): At 3 months the median score was +1 (IQR 0 to +2), the mean 0.84. At 12 months the median score was +2 (IQR+1 to +3), the mean 1.66. At 18 months the median score was +3 (IQR+3 to +3), the mean 2.33. An increase in hair growth of >+1 was experienced in 71 patients (56%) at 3 months, 43 (78%) at 12 months, and 9 (90%) at 18 months.

Early responders: Sixty-seven patients (53%) achieved >+1 score by 3 months of treatment. Of these, 40% achieved a +2, and 22% a +3. Ten patients (15%) were paediatric. The mean age of disease onset was 25.6 years (range 2-63) and mean duration of disease 9.8 years (range 1-40). Fifteen patients (22%) had AT/AU. Twenty-two patients (32.8%) were able to cease concomitant immunosuppressant medication.

Late responders: Thirty-one patients (24%), achieved >+1 score after 6 months of treatment. At 6 months 8 had a score of 0, 17 a score of >+1, including 2 with CR. At 9 months 20 had a score of >+1 with 4 in CR. By 15 months all patients in this group were >+1 and 10 had achieved CR. The mean age of disease onset was 21 years (range 1-56) and mean duration of disease 9.3 years (range 1-37). Ten (32%) had AT/AU. Seven (22.5%) were able to cease concomitant immunosuppressant medication.

Prolonged Disease Duration: Thirty-eight patients were included whose current AA episode had persisted for >10 years. The mean disease duration was 19.9 years (range 10-40). Fourteen had AT/AU and 5 were paediatric cases. Eleven achieved a CR with tofacitinib, 21 were early responders, 10 were late responders, 2 relapsed and 6 never responded. Seven ceased concomitant immunosuppressant medication, 5 started prednisolone and 18 were given intralesional triamcinolone.

Relapses: Twenty-eight patients (22%) experienced a relapse. Fifteen were early responders, 9 were late responders. Nine relapsed after having initially achieved CR that had been sustained for 3-12 months. The relapse was salvaged in 23 patients with continued treatment but 5 were unable to regain disease control and were considered secondary treatment failures. Five had AT/AU. Ten were paediatric patients. All but eight had a dose escalation. Five had a short course of oral prednisolone and 3 stopped treatment.

Treatment Failures

Primary: Twenty-four patients (19%) failed to respond to treatment. The mean age of disease onset was 25 years (range 2-60) and the mean duration of disease 9 years (range 2-39). Four were paediatric. Ten (42%) had AT/AU. At the time of writing this application, 17 remain on treatment. Three have had continuous treatment out to 15 months with no evidence of hair regrowth and 3 have ceased concomitant immunosuppressant medications. Seven ceased treatment without achieving regrowth.

Secondary: Five patients out of 28 who experienced a relapse while on treatment failed to respond and were considered a secondary failure. The mean age of disease onset was 9 years (range 3-13) and mean disease duration 18.6 years (4-31). None had AT/AU. Two were paediatric. None stopped treatment and 1 ceased concomitant immunosuppressant medications. Three reached 15 months and 1 reached 18 months. Only 1 patient reached CR. Rescue therapy included dose escalation, intralesional triamcinolone and oral prednisolone. Of these, 2 had deteriorated, 1 was unchanged and 2 had slightly improved from baseline.

Comparison of Sublingual Versus Orally Administered Tofacitinib

A break-down of subjects treated with sublingual minoxidil compared to those treated with orally administered tofacitinib is provided in Tables 6 and 7. The mean dose of tofacitinib sublingually (4.64 mg) was lower than orally administered (5.22 mg) tofacitinib. Comparable efficacy at a lower dose was observed with sublingual minoxidil compared to orally administered minoxidil without the requirement for additional drugs administered with orally administered tofacitinib to reduce hepatic metabolism of tofacitinib.

Tofacitinib Monotherapy

Fifty-six patients (44%) were not taking any other immunosuppressant medications when they started tofacitinib. There were 34 females and 22 males, 10 were pediatric, the mean age was 36 years (range 11-68), with a mean age of onset of disease of 25 years (range 2-63) and a mean duration of disease of 10.5 years (range 1-40). Twenty-nine of these patients had patchy disease, whilst 27 had AT/AU. Eighteen of these patients achieved a CR. Twenty-nine (51.7%) were considered early responders, 11 (19.6%) were late responders, 15 were primary failures (26.7%), and 1 was a secondary failure. Fifteen (26.7%) of these patients were given rescue oral prednisolone at some point with a mean daily dose of 16.8 mg (range 10-25) for a mean period of 5.5 months (range 2-11). Twenty-one (37.5%) of these patients were given intralesional steroid injections at some point with a mean of 4 injections (range 1-8).

TABLE 3

Percentage of responders with orally administered tofacitinib

| Time point | Mean Dose mg (Range) Tablet | Score +1 | Score +2 | Score +3 | Total responders | Total non-responders |
| --- | --- | --- | --- | --- | --- | --- |
| 3 months (n = 39) | 4.19 (1-10) | 7 | 8 | 7 (18%) | 22 (56%) | 17 (44%) |
| 6 months (n = 36) | 4.96 (2-15) | 4 | 7 | 10 (27%) | 21 (58%) | 15 (42%) |
| 9 months (n = 25) | 5.58 (2-15) | 3 | 4 | 12 (48%) | 19 (76%) | 6 (24%) |
| 12 months (n = 21) | 5.63 (2-15) | 1 | 5 | 11 (52%) | 17 (81%) | 4 (19%) |
| 15 months (n = 16) | 6.90 (1.25-20) | 1 | 2 | 9 (56%) | 12 (75%) | 4 (25%) |
| 18 months (n = 7) | 6.07 (5-10) | 0 | 1 | 5 (71%) | 6 (86%) | 1 (14%) |

TABLE 4

Percentage of responders with sublingually administered tofacitinib

| Time point | Mean Dose mg (Range) Sublingual | Score +1 | Score +2 | Score +3 | Total responders | Total non-responders |
| --- | --- | --- | --- | --- | --- | --- |
| 3 months (n = 88) | 3.73 (2-5) | 21 | 20 | 8 (9%) | 49 (53%) | 41 (46.5%) |
| 6 months (n = 74) | 4.48 (2.5-10) | 18 | 17 | 15 (20%) | 50 (68%) | 24 (32%) |
| 9 months (n = 53) | 4.71 (2.5-10) | 13 | 12 | 14 (26%) | 39 (74%) | 14 (26%) |
| 12 months (n = 34) | 6.25 (2.5-12.5) | 8 | 11 | 11 (32%) | 29 (85%) | 5 (15%) |
| 15 months (n = 15) | 6.81 (2.5-10) | 3 | 5 | 6 (40%) | 14 (93%) | 1 (7%) |
| 18 months (n = 3) | 5.00 (2.5-7.5) | 0 | 0 | 3 (100%) | 3 (100%) | 0 |

Discussion

Tofacitinib (dose range 1-20 mg) was well tolerated, arrested hair loss and stimulated regrowth in the overwhelming majority of patients. Response to treatment was noted as early as 3 months. Most had a partial response at 6 months and a CR by 18 months. Relapse was seen in 28 patients (22%). Ten patients went on to respond and three ceased treatment. Primary failure was seen in 24 patients (19%) and 7 of these ceased treatment with tofacitinib.

Our study included both children and adults, as well as patients with prolonged disease duration (up to 40 years). AA that remains active after 12 months follows a relapsing and remitting course and it is therefore difficult to ascertain with certainty when exactly the disease process has completely arrested. Patients often return with new disease long after they have achieved what appears to be complete remission. In light of this clinical experience, the disease duration from the first date of reported disease was recorded rather than from the current episode as this reflects better the true clinical course of the disease. Thirty-eight of our patients (30%) had disease duration of >10 years. Of these, 11 achieved a CR, 21 were early responders, and 10 were late responders. Therefore 81.6% of these patients had regrowth with tofacitinib. Likewise, 25 patients (71%) with AT/AU achieved a response and 13 (37%) achieved a CR.

Tofacitinib is not reimbursed for alopecia areata in Australia and the cost to patients for sixty 5 mg tablets is approximately AUD $1342. For some patients, the distress associated with alopecia areata would justify this expense, but for many patients this is simply unaffordable. The sublingual composition as described herein provides a more cost effective option of treating and prevent hair loss conditions such as alopecia areata.

Side effects were infrequent and mild. One patient developed asymptomatic hepatic transaminitis that failed to improve with dose reduction and led to eventual treatment discontinuation. The patient was later diagnosed with non-alcoholic steatohepatitis.

Conclusion

Tofacitinib was well tolerated and highly effective although prolonged treatment may be required. The relatively high number of late responders seen in the cohort indicate that tofacitinib treatment should not be deemed to have failed until at least 12 months of continued treatment. Tofacitinib can be administered sublingually with comparable efficiency to orally administered doses administered with other components to reduce tofacitinib hepatic metabolism Example 2: Sublingual Tofacitinib for Alopecia Areata: A Roll-Over, Placebo-Controlled Clinical Trial and Study of Pharmacokinetics Alopecia areata (AA) is the most common autoimmune disease in man with an incidence of 0.2% and estimated lifetime risk of 2.1%. Acute AA occurs with 1-5 circular patches of alopecia that develop in close succession and spontaneously regrow within 6-12 months. When AA persists beyond 12 months it is defined as chronic AA. Approximately 30% of patients develop chronic AA with the serial development of multiple patches of alopecia over many years. Roughly 50% of patients with chronic AA progress to alopecia totalis (AT) or alopecia universalis (AU). There is significant impact on health-related quality-of-life (QOL).

A systematic review of all systemic treatments for AA showed no reliably effective evidence-based treatments for chronic AA (Lai et al. 2019). Clinicians currently approach rapidly progressive AA through a combination of systemic corticosteroids and steroid-sparing agents, for which high quality evidence remains scarce.

To date, there are no placebo-controlled clinical trials investigating systemic tofacitinib in alopecia areata. Furthermore, sublingual administration has not been reported.

The aims of this study was to quantify the efficacy of sublingual tofacitinib in patients with moderate to severe, treatment-resistant AA and to measure the pharmacokinetics of sublingual tofacitinib, a novel form of administration for this drug, through a roll-over clinical trial.

In the initial study, 32 participants (16 who received cyclosporine and 16 who received placebo) were enrolled. Compared with placebo, the cyclosporine group had a greater proportion of participants achieving at least a 50% reduction in Severity of Alopecia Tool (SALT) score (31.3% vs 6.3% [p=0.07]) and greater proportion of participants achieving a 1-grade improvement in eyelash (18.8% vs 0% [p=0.07]) and eyebrow (31.3% vs 0% [p=0.02]) scale score (Lai et al. 2019b). The response approached but did not reach a statistically significant difference between cyclosporine and placebo (Lai et al. 2019b).

Methods

Figure 7:
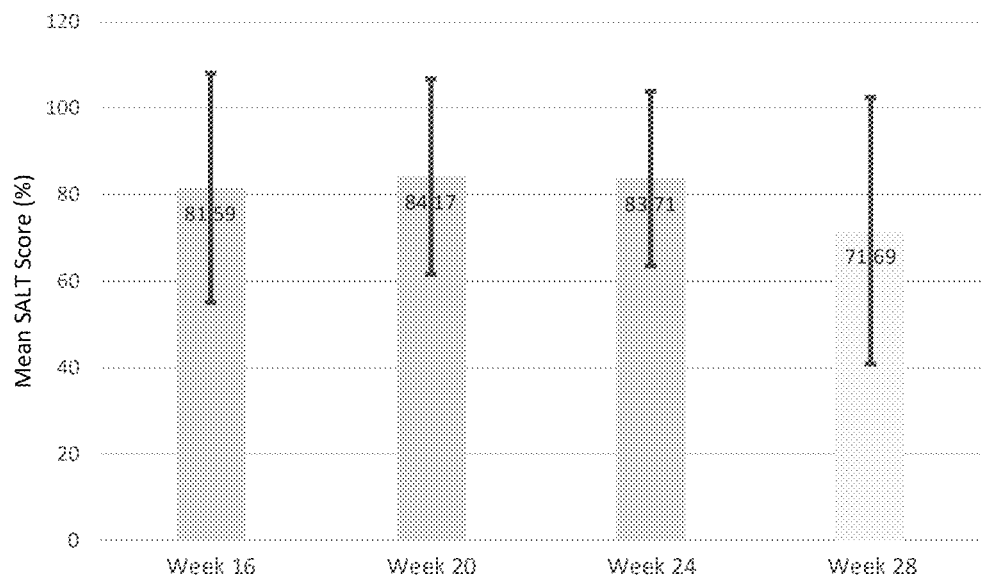
FIG. 7: Mean SALT score over time in patients receiving tofacitinib. Error represent standard deviations.

Trial design: This was a single-centre, open-label, roll-over, placebo-controlled clinical trial conducted in Melbourne, Australia (FIG. 7). The first part of this trial involved a 3-month randomised, parallel-group, placebo-controlled study investigating the efficacy of cyclosporine compared to placebo in patients with moderate to severe AA; results of which have been published (Lai et al. 2019b). All responders (a minimum 50% reduction in SALT score from Week 0) to cyclosporine/placebo at Week 12 continued on a 3-month extension of the same allocated treatment in this clinical trial, while all non-responders rolled-over to receive open-label tofacitinib for 3 months after a 4-week washout period.

Participants: Eligible participants were all adults aged 18 to 65 years with moderate to severe AA who had completed Week 12. Exclusion criteria were: pregnancy and lactation; non-adherence to use of highly effective contraception throughout the study and for at least 30 days after the last dose of medication; concomitant use of other hair-promoting treatments; tofacitinib use within 12 weeks of the first dose of study drug; history of any lymphoproliferative disorder, human immunodeficiency virus (HIV), tuberculosis, hepatitis B or hepatitis C; active herpes simplex infection; hypersensitivity to the study medication; and any medical abnormality that may increase the risk of study participation.

Interventions: Tofacitinib was supplied in 5.5 mm diameter translucent tablets for sublingual administration. Each tablet contained 5 mg of tofacitinib citrate. Participants continuing on the same initial treatment (cyclosporine 4 mg/kg/day or placebo) remained blinded.

Study procedures: At each visit, the following assessments were completed: SALT score, eyelash and eyebrow scales, physical examination, blood biochemistry, urine pregnancy test for females of child-bearing potential, photography, adverse event monitoring and checking concomitant medications.

SALT scores represent a total percentage of scalp hair loss, through visual summation of patches of complete hair loss across the left, right, posterior and superior scalp. The eyelash and eyebrow assessment scales are a categorical spectrum from 0 (no eyelashes/eyebrows) to 3 (normal eyelash/eyebrows). Participants completed 2 QOL questionnaires at each visit, the disease-specific instrument, Alopecia Areata Symptom Impact Scale (AASIS) (13) and the generic instrument, Assessment of Quality of Life-8D (AQoL-8D) (14).

Pharmacokinetics analysis: Blood samples were collected from tofacitinib-arm participants at Week 16 and 28 at pre-dose (0 hours), 0.5, 1, 3 and 24 hours. Blood samples were left to coagulate at room temperature for 20 minutes before centrifuging at 3500 rotations per minute for 15 minutes. The resulting separated plasma was extracted and stored at −20 degrees Celsius prior to processing using the liquid chromatography tandem mass spectrometry (LC MS/MS) method.

For the quantification of tofacitinib concentration in samples, 10 microlitres (μls) of each sample was injected into a Shimadzu HPLC system (Shimadzu, Kyoto, Japan) using an Ascentis® Express C18 column (Sigma-Aldrich, Castle Hill, New South Wales, Australia) equipped with a Phenomenex SecurityGuard™ C18 guard column (Phenomenex Inc., Lane Cove, New South Wales, Australia). The mobile phase consisted of (A) 5 mM ammonium acetate pH 4 and (B) methanol. The gradient profile developed was: 0-2.0 min, 90% A, 10% B; 2.0-3.0 min, 30% A, 70% B; 3.0-4.0 min, 90% A, 10% B. A Shimadzu LC MS/MS-8050 triple quadrupole mass spectrometer (Shimadzu, Kyoto, Japan) was used to perform the mass spectrometry. MS/MS analysis was performed in positive ion mode using electrospray ionization conditions. Stock solutions of tofacitinib were prepared in methanol (1 mg/mL). Calibration curves for tofacitinib were obtained by preparing working standard solutions. The calibration standard range was linear between 0.5 to 100 ng/mL ($R2=0.9978$). The lower limit of quantification was 0.5 ng/mL. The maximum observed plasma concentration (Cmax) and time to Cmax (tmax) of tofacitinib was estimated directly from the experimental data.

Outcomes: The primary objective of this study was to evaluate the efficacy of sublingual tofacitinib at Week 28 compared to baseline at Week 16 in patients with moderate to severe AA aged 18 to 65 years who had failed to respond to initial therapy with cyclosporine or placebo. Efficacy endpoints included: proportion of participants achieving a low, medium, good and high-grade response (15 to 29%, 30 to 49%, 50 to 75% and 75 to 100% reduction in SALT score respectively); mean change in SALT score; and proportion of participants achieving at least 1 grade improvement in eyelash and eyebrow assessment scales.

The secondary objective was to evaluate the effect of tofacitinib on QOL at Week 28 through a change from baseline in AQoL-8D and AASIS scores.

Statistical Analysis: Statistical analyses were performed using Stata 12 software. A per protocol analysis was performed. Descriptive statistics were summarised using means and standard deviations as there were no significant outliers. As this was a pilot clinical trial, the efficacy data presented may help calculate future sample sizes required for statistical significance. Mann-Whitney U tests for non-normally distributed continuous data and chi-squared tests for categorical data were performed to compare groups. Statistical significance was defined as $p<0.05$.

Ethical approval: Ethical approval was from Bellberry Human Research Ethics Committee (HREC No. 2018-08-607), Committee E (EC00450).

Results

Figure 3:
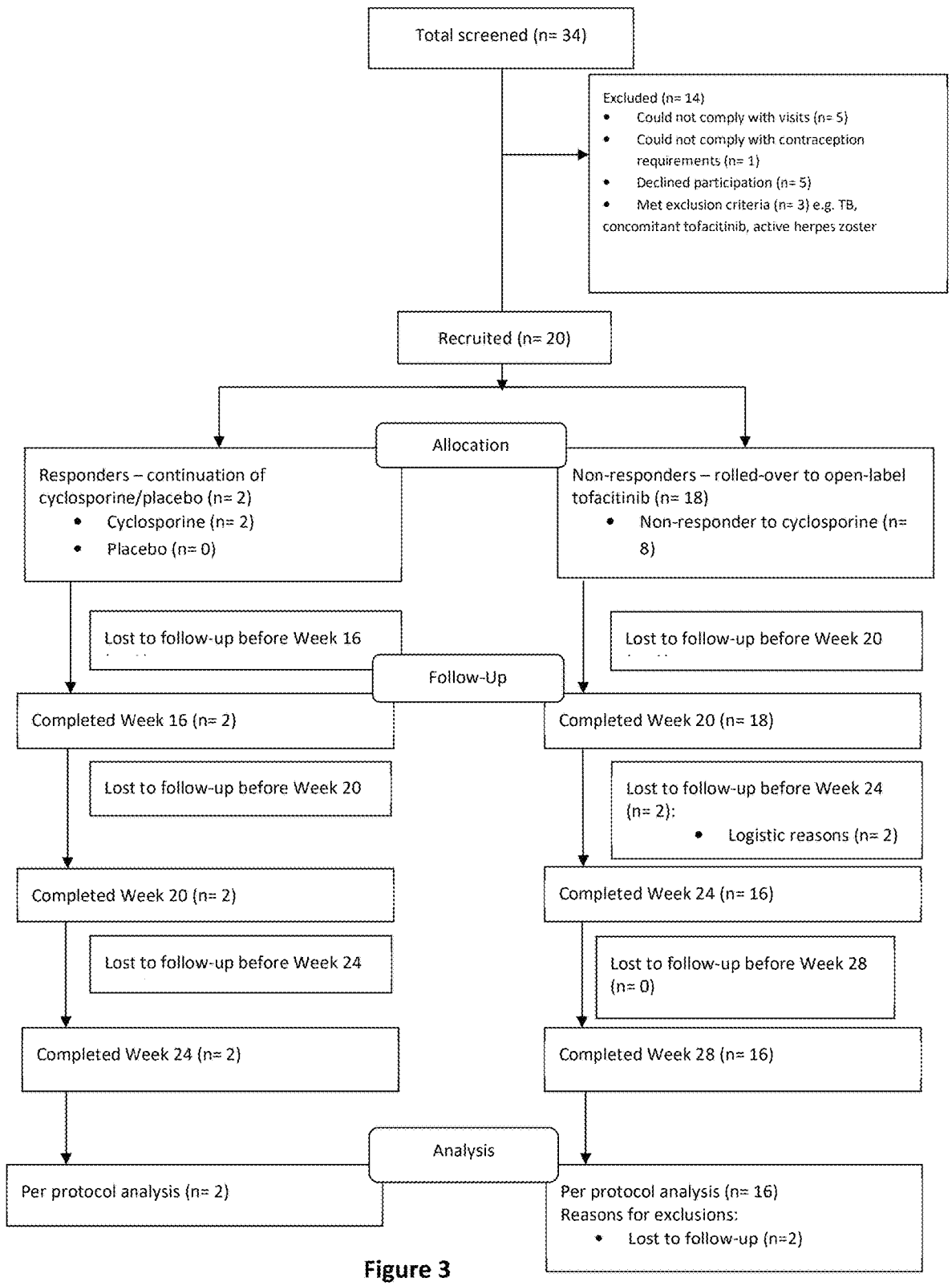
FIG. 3: Shows a flow diagram of allocation, follow-up and analysis of participants in the Example 2 study.

Participant recruitment: A total of 20 patients enrolled in the extension phase of the study; 2 continued to receive initial treatment (cyclosporin) for a further 12 weeks, while 18 were rolled-over to receive tofacitinib (FIG. 3).

Participant demographics: The mean age for participants in the roll-over tofacitinib arm was 45.11 years and the mean age at onset of first episode of AA was 27.72 years (Table 5). The mean duration of current episode of AA was 7.79 years and mean percentage scalp hair loss by SALT score at baseline was 86.01%. The majority of participants in the roll-over tofacitinib arm had AT/AU (72.22%), with 100% or some body hair loss (83.33%), nail involvement (44.44%), no eyelashes (55.56%) and no eyebrows (61.11%).

TABLE 5

Baseline demographic and clinical characteristics of all randomized participants

| | | | |
|---|---|---|---|
| Age (years) | 44 (14.96) | 34 (5) | 45.11 (15.28) |
| Sex (female) | 15 (75%) | 1 (50%) | 14 (77.78%) |
| Age at onset of first episode of AA (years) | 26.75 (14.92) | 18 (11) | 27.72 (14.99) |
| Age at onset of current episode of AA (years) | 37 (15.24) | 32.5 (5.5) | 37.50 (15.89) |
| Duration of current episode of AA (years) | 7.13 (11.48) | 1.25 (0.25) | 7.79 (11.92) |
| Mean percentage scalp hair loss by SALT score at baseline (%) | 81.59 (26.53) | 41.75 (19.75) | 86.01 (23.30) |
| Pattern of scalp hair loss, n (%) | | | |
| AT | 6 (30%) | 0 (0%) | 6 (33.33%) |
| AU | 8 (40%) | 1 (50%) | 7 (38.89%) |
| Patchy | 6 (30%) | 1 (50%) | 5 (27.78%) |
| Body hair loss, n (%) | | | |
| 100% loss | 8 (40%) | 1 (50%) | 7 (38.89%) |
| No loss | 3 (15%) | 0 (0%) | 3 (16.67%) |
| Some loss | 9 (45%) | 1 (50%) | 8 (44.44%) |
| Nail involvement | 10 (50%) | 2 (100%) | 8 (44.44%) |
| History of AT/AU at any time | 16 (80%) | 2 (100%) | 14 (77.77%) |
| Duration of AT/AU, n (%) | | | |
| ≤2 years | 8 (50%) | 2 (100%) | 6 (42.89%) |
| >2 years | 8 (50%) | 0 (0%) | 8 (57.14%) |
| Medical history, n (%) | | | |
| Atopy | 6 (30%) | 0 (0%) | 6 (33.33%) |
| Endocrine | 2 (10%) | 0 (0%) | 2 (11.11%) |
| Psychological illness | 2 (10%) | 0 (0%) | 2 (11.11%) |
| Family history of AA | 2 (10%) | 0 (0%) | 2 (11.11%) |
| Score of 0 (no eyelashes) on eyelash assessment scale | 10 (50%) | 0 (0%) | 10 (55.56%) |
| Score of 0 (no eyebrows) on eyebrow assessment scale | 11 (55%) | 0 (0%) | 11 (61.11%) |

AA, alopecia areata; AT, alopecia totalis; AU, alopecia universalis.
Data are means (SD) or numbers (%)

Figure 4:
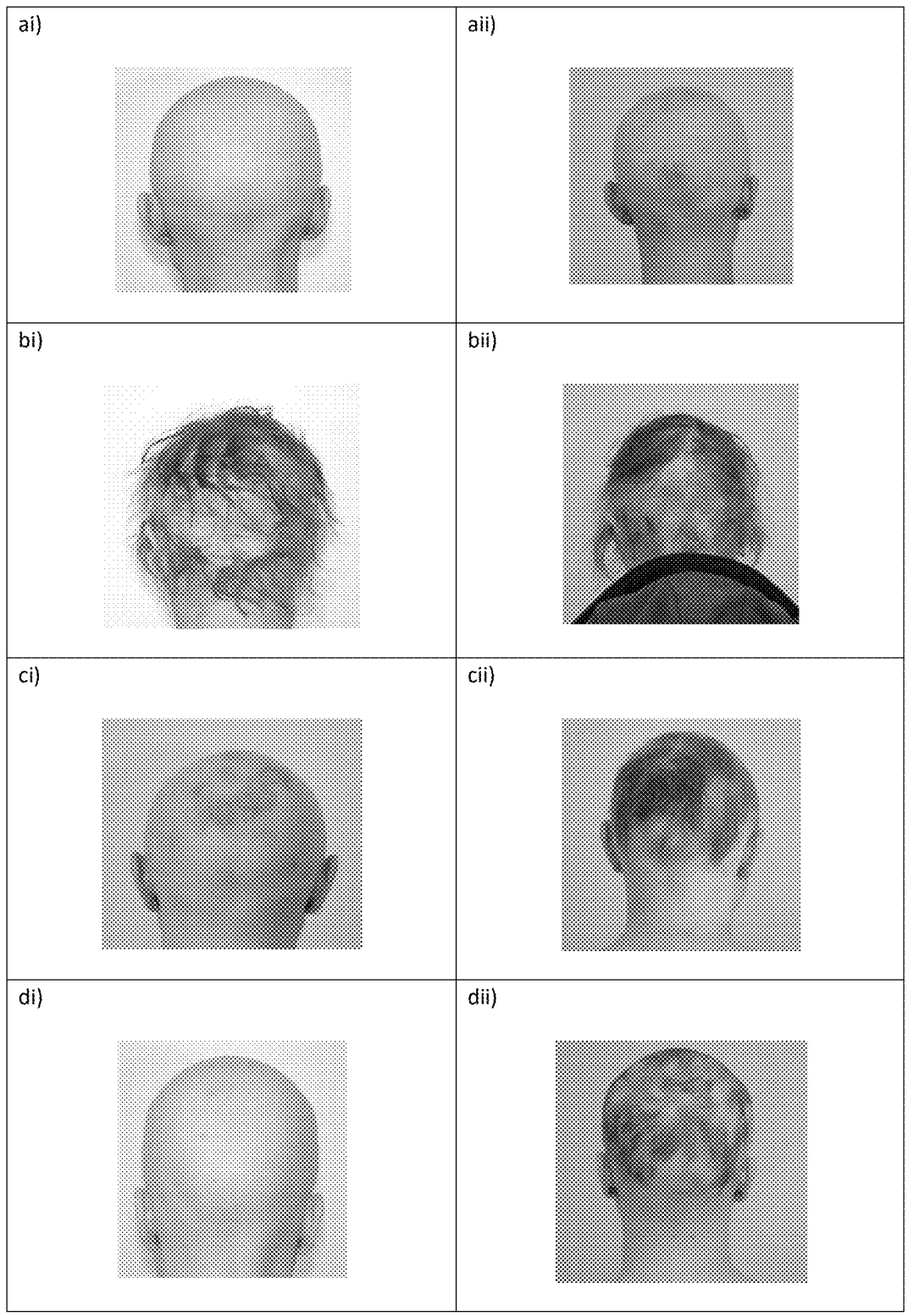
FIG. 4: Provides an example of the treatment response observed in patients receiving sublingual tofacitinib. a) Shows a low grade response. ai) Patient at week 16. aii) The same patient at week 28 after 3 months or sublingual tofacitinib. b) Shows a medium grade response. bi) Patient at week 16. bii) The same patient at week 28 after 3 months or sublingual tofacitinib. c) Shows a good grade response. ci) Patient at week 16. cii) The same patient at week 28 after 3 months or sublingual tofacitinib. d) Shows a high grade response. di) Patient at week 16. dii) The same patient at week 28 after 3 months or sublingual tofacitinib.

Treatment response: Total treatment response to sublingual tofacitinib was 37.5% (6/16) (Table 6). 1 participant (6.25%) receiving sublingual tofacitinib achieved a high grade response (>75% reduction in SALT score); 1 participant (6.25%) achieved a good grade response (50-75%); 1 participant (6.25%) achieved a medium grade response (30-49%); and 3 participants (18.75%) achieved a low grade response (15 to 29%) at Week 28 compared to Week 16 (FIG. 4). No participants achieved a 100% reduction in SALT score at Week 28. The mean reduction from baseline of SALT score at Week 28 was 15.57%. 37.5% (6/16) of participants receiving tofacitinib achieved at least a 1 grade improvement in eyelash assessment scale and 50% (8/16) of participants achieved at least a 1 grade improvement in eyebrow assessment scale. The 2 continuation participants on cyclosporine did not achieve significant incremental improvement at 6 months compared the initial 3 months.

TABLE 6

Summary of results for primary and secondary objectives at Week 28

| Primary Objective - Efficacy of sublingual tofacitinib | |
|---|---|
| Mean reduction from baseline (Week 16) of SALT score at Week 28 | 15.57 (23.41) |
| Treatment Response (Reduction in SALT score at Week 28) | |
| Low grade respondents (15-29%) | 3/16 (18.75%) |
| Medium grade respondents (30-49%) | 1/16 (6.25%) |
| Good grade respondents (50-75%) | 1/16 (6.25%) |
| High grade respondents (75-100%) | 1/16 (6.25%) |
| Total Treatment Response | 6/16 (37.5%) |
| Proportion of participants achieving at least 1 grade improvement in eyelash assessment scale at Week 28 | 6/16 (37.5%) |
| Proportion of participants achieving at least 1 grade improvement in eyebrow assessment scale at Week 28 | 8/16 (50%) |
| Secondary Objective - Quality of life measurements | |
| Mean change from baseline in Assessment of Quality of Life-8D (AQoL-8D) score at Week 28 (n = 13) | −0.0148 (0.0515) |

TABLE 6-continued

Summary of results for primary and secondary objectives at Week 28

| | |
|---|---|
| Mean change from baseline in Alopecia Areata Symptom Impact Scale (AASIS) score at Week 28- Global Symptom Impact Score[2] (n = 14) | −0.1306 (0.1252) |
| Mean change from baseline in Alopecia Areata Symptom Impact Scale (AASIS) score at Week 28- Scalp Hair Loss Score[3] (n = 14) | −2.2142 (2.3916) |

Data are mean (standard deviation) or proportion (percentage).

Effect of tofacitinib on QOL: Participants receiving tofacitinib had improved QOL at Week 28 compared to baseline, across a number of QOL measurements, including a 0.0148 improvement in overall weighted QOL as measured by AQoL-8D; a 0.1306 improvement in Global Symptom Impact score as measured by AASIS; and a 2.2142 reduction of the severity of their scalp hair loss as measured on the AASIS.

Safety and tolerability: There were no serious adverse events experienced by participants receiving open-label tofacitinib. There were no withdrawals secondary to adverse events. There were no clinically significant changes in blood biochemistry in the tofacitinib group.

Figure 5:
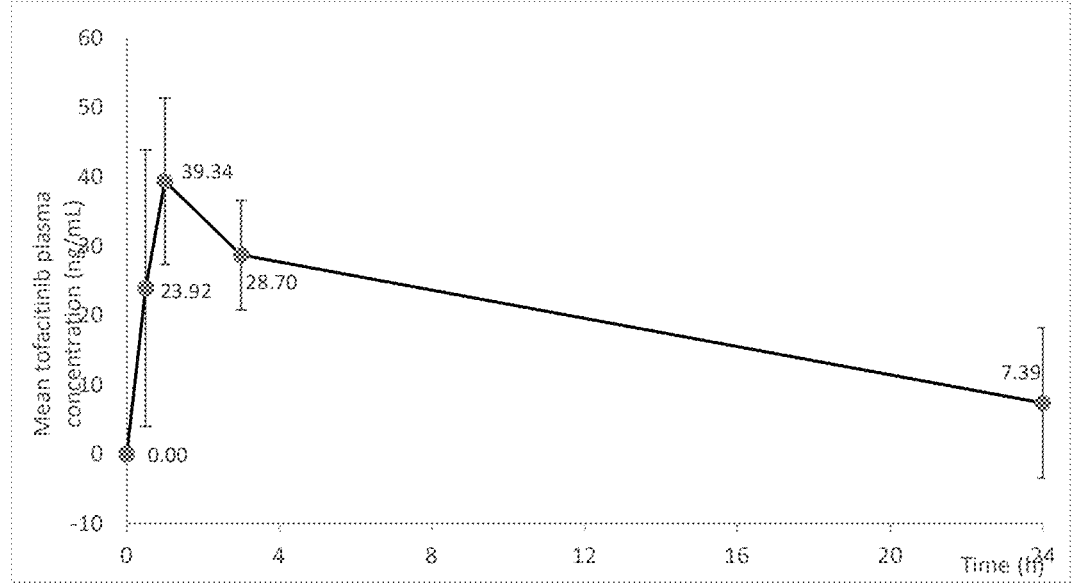
FIG. 5: Shows the mean tofacitinib plasma concentration-time profiles. a) Week 16. Roll-over visit into tofacitinib arm. Mean plasma concentration levels were calculated prior to first dose (0 hour) and at 0.5 hour, 1 hour, 3 hours and 24 hours after dose. b) Week 28. End of treatment visit. Mean plasma concentration levels were calculated prior to the final in-clinic dose (0 hour) and at 0.5 hour, 1 hour, 3 hours and 24 hours after dose. Error bars represent standard deviations.
Figure 5:
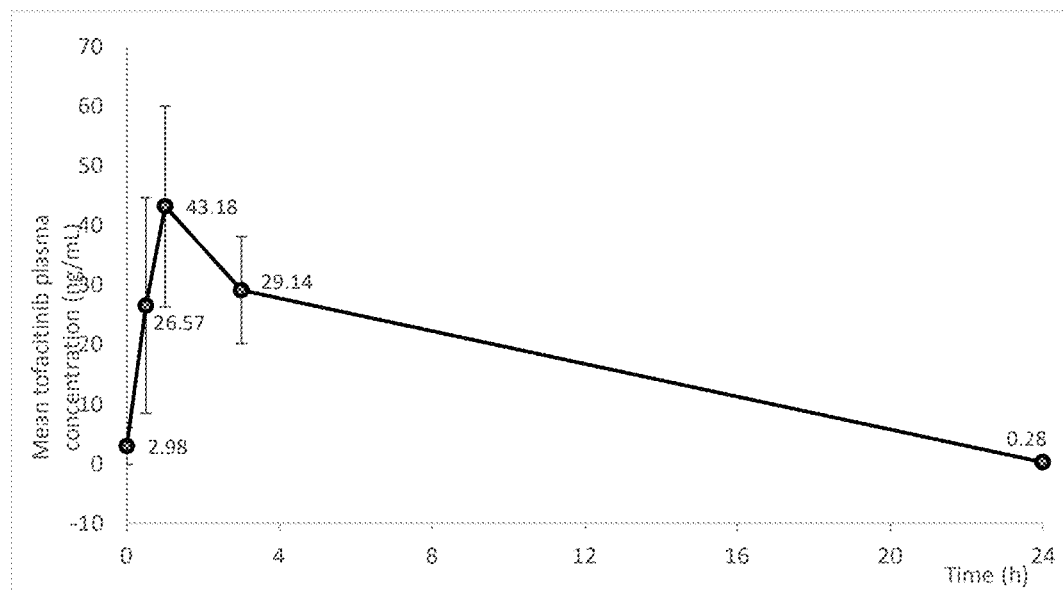
Figure 6:
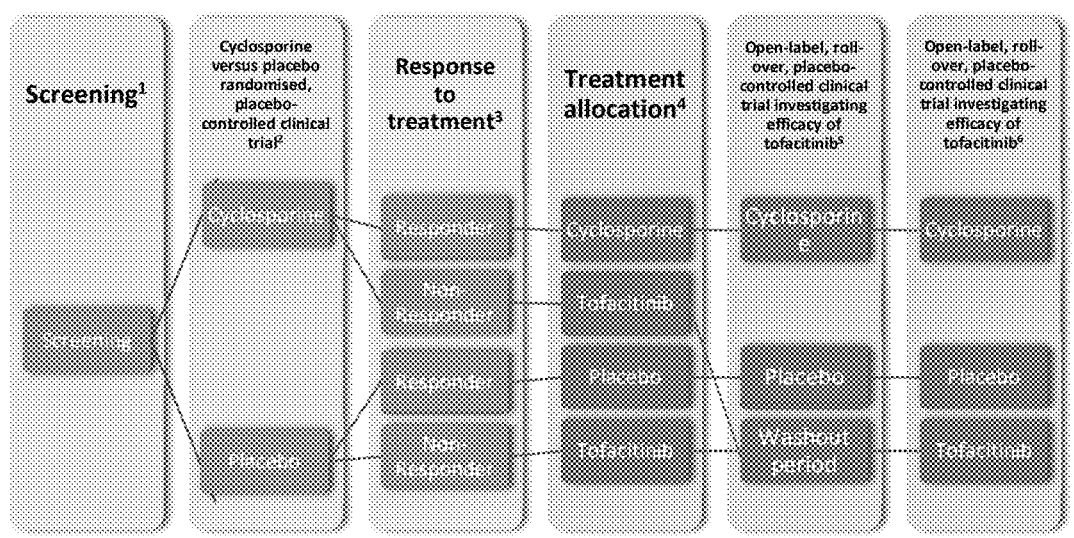
FIG. 6: Shows the study design of Example 2. 1) Screening was up to 35 days prior to randomization; week-5 to 0 (Visit 1). 2) Conducted over 3 months; week 0 to week 12 (Visits 2, 3, 4, 5). 3) Response to cyclosporine/placebo was evaluated at week 12 (Visit 5). 4) Responders continued immediately on the same treatment for 3 months. Non-responders rolled-over to open-label tofacitinib after a 4-week washout period. 5) Cyclosporine/placebo arms continued 3 months of treatment over weeks 12, 16, 20, 24 (Visits 5, 6, 7 and 8), respectively. The tofacitinib arm commenced treatment at week 16 (Visit 6) after a 4-week washout period, and continued treatment over weeks 20, 24, 28 (Visits 7, 8, 9), respectively. 6) Response was evaluated at week 24 (Visit 8) for the cyclosporine/placebo arms and week 28 (Visit 9) for the tofacitinib roll-over arm.

Pharmacokinetics: A total of 72 plasma samples were analysed. At Week 16, 18 patients were analysed and at Week 28, 15 patients were analysed. The precision and accuracy table of the developed assay is in Table 7. The maximum plasma concentration of sublingual tofacitinib (Cmax) was on average 43.18 ng/ml. The average time (tmax) to maximum plasma concentration was 1-hour post administration (FIG. 5).

TABLE 7

Precision and accuracy of LC MS/MS assay for quantification of tofacitinib in human plasma

| Target Concentration (ng/mL) | Measured concentration (ng/ml) Mean ± SD (n = 5) | Precision (%) | Accuracy (%) |
|---|---|---|---|
| 0.5 | 0.46 ± 0.024 | 5.34 | 91.51 ± 4.89 |
| 100 | 107.97 ± 1.073 | 0.99 | 107.97 ± 1.073 |

This table indicates the robustness and reliability of the methodology in quantifying tofacitinib in human plasma over the concentration range of 0.5 to 100 ng/ml.

At Week 16, following the first dose of tofacitinib, 4 patients achieved tmax at 0.5 hour, 10 patients at 1 hour and 4 patients at 3 hours. At Week 28, prior to the last dose of tofacitinib, 10 patient samples had trace levels of tofacitinib (range: 0.5-10.0 ng/ml). One patient achieved tmax at 0.5 hour, 11 patients at 1 hour and 3 patients at 3 hours.

At both Weeks 16 and 28, tofacitinib plasma levels had significantly reduced by 24 hours. Patients at Week 16 had an average plasma concentration of 7.39 ng/mL at 24 hours, likely representing a spuriously elevated result given the range of time the nocte dose was taken, while patients at Week 28 had negligible levels (0.28 ng/mL) as they did not receive a nocte tofacitinib dose.

Discussion

The efficacy of sublingual tofacitinib was investigated in patients with moderate to severe AA, unresponsive to either cyclosporine (8/18) or placebo treatment (10/18) for 3 months prior. Sublingual tofacitinib patients achieved a 37.5% total response rate compared to 31.3% with cyclosporine 4 mg/kg/day and 6.3% with placebo in the initial study. A >50% reduction in SALT score was achieved by 12.5% of patients with sublingual tofacitinib, versus 31% of cyclosporine and 6% with placebo. The mean reduction from baseline of SALT score was 15.57% compared to 14.80% with cyclosporine and 2.30% with placebo. With sublingual tofacitinib, 37.5% achieved at least 1 grade improvement in eyelash assessment scale compared to 18.8% with cyclosporine and 0% with placebo. 50% achieved at least 1 grade improvement in eyebrow assessment scale at the end of 3 months with tofacitinib compared to 31.3% with cyclosporine and 0% with placebo.

Three open-label trials for oral tofacitinib have been published (Crispin et al. 2016; Jabbari et al. 2018; Almutairi et al. 2019). One trial investigated oral tofacitinib 5 mg twice daily for 3 months and found 32% of patients achieving a 50% or greater reduction in SALT score (Crispin et al. 2016). Compared to the current trial, their cohort consisted of shorter median duration of current episode of AA (5 years versus 7.79 years). Furthermore, 44.44% (8/18) of patients receiving tofacitinib were rolled-over from the first clinical trial as cyclosporine-resistant participants, implying greater treatment difficulty due to failure of initial systemic therapy.

A second trial of 12 patients investigated oral tofacitinib initially at 5 mg twice daily for at least 1 month, then 15 mg daily for at least another month, and finally 10 mg twice daily if there remained no terminal hair regrowth. All but one patient required escalation to the maximum dose of tofacitinib and at least 6 months of treatment for response (Jabbari et al. 2018), suggesting doses twice as high and durations twice as long as that investigated in the current study are required to achieve clinical response.

The third study compared oral tofacitinib 5 mg twice daily with oral ruxolitinib 20 mg twice daily for 6 months (Almutairi et al. 2019). Response rates for tofacitinib and ruxolitinib respectively were 64.9% and 68.4%. Again, this was a cohort of relatively short duration of disease −2.61 years—in comparison to trial patients in the current study.

This is the first study to investigate sublingual delivery of tofacitinib. Oral tofacitinib achieves a mean maximum plasma concentration of 40.5 ng/mL at 0.5 to 1 hour (Lamba et al. 2016; Dowty et al. 2014; Tan et al. 2013; Villasante et al. 2015). Sublingual tofacitinib achieves a mean maximum plasma concentration of 43.18 ng/mL at 1 hour. By 24 hours, tofacitinib plasma levels were negligible, similar to oral tofacitinib. These findings suggest no significant superiority of sublingual administration compared to oral in terms of maximum plasma concentrations achieved and time to maximum concentration. The approximate duration for the plasma concentration to halve from 29.14 ng/ml to 14.6 ng/ml is 11 hours (FIG. 5b). This is almost four times the reported elimination half-life of oral tofacitinib (3 hours) (Lamba et al. 2016; Dowty et al. 2014; Tan et al. 2013; Villasante et al. 2015).

In this study the tofacitinib group was not blinded or randomised. This occurred as treatment-resistant patients were recruited in the roll-over design of the study and because randomisation had already occurred to attain a placebo group in the initial clinical trial.

The findings are generalisable to a cohort of moderate to severe AA patients (mean percentage scalp hair loss of 86.01% at baseline) and long duration of current episode of AA (mean duration 7.79 years). A total response rate of 37.5% was found. Of note, two patients who achieved >50% reduction in SALT score had a mean 60.3% reduction in SALT score, suggesting that patients with shorter disease duration and shorter current episode of AA may have fast and favourable response. Although there was no superiority of sublingual administration compared to oral in terms of maximum plasma concentrations achieved and time to maximum concentration, the estimated elimination half-life of sublingual tofacitinib (11 hours) implies it remains active in the body significantly longer than the oral form.

Sublingual tofacitinib is a valid second-line therapeutic option for patients with severe AA and may be utilised as a promising alternative in resistant disease.

Example 3: Measurement of the Amount of Tofacitinib in Tofacitinib Citrate (5 Mg) Mini-Tablets This study assessed the quantity of tofacitinib in tofacitinib citrate tablets used in Example 2. A robust and reliable HPLC-UV assay for quantifying tofacitinib was developed and validated. Using this validated assay, the amount of tofacitinib was assessed in 6 tofacitinib citrate tablets. The concentration was determined to be 5.4±0.3 mg (mean±SD).

Methods

Preparation of samples for HPLC validation: A stock solution of tofacitinib was first prepared in methanol (1 mg/mL). Working standard solutions with concentrations of 10, 20, 50, 100 and 200 µg/mL were prepared by serial dilution of the stock solution in methanol:$H_2O$ (1:1). Low- and high-quality control (QC) solutions of 10 and 200 µg/mL, used for determination of the precision and accuracy of the assay, were prepared in the same manner using an independently prepared stock solution. Calibration and QC samples were prepared by spiking a 20 µL aliquot of the working solutions of tofacitinib into 180 µL of methanol:$H_2O$ (1:1) to achieve concentrations of 1, 2, 5, 10 and 20 µg/mL. To quantify the amount of tofacitinib in each tablet, a volume of 10 mL of methanol:$H_2O$ (1:1) was used to dissolve each tablet. Once the tablet had completely dissolved (approximately 15 minutes), 10 µL of the solution was transferred into an Eppendorf tube and diluted by adding 990 µL of methanol:$H_2O$ (1:1). Each sample was centrifuged for 5 min at 1000 g. An aliquot of 150 µL of the supernatant was then collected and analysed by the HPLC method described in the following section.

QC samples (n=4-5) at each concentration were quantified for tofacitinib to determine the intraday assay precision and accuracy. Precision was expressed as relative standard deviation (%) and accuracy was calculated as the difference between the measured and expected concentrations, which was expressed as a percentage.

HPLC analysis: A Phenomenex® Gemini C18 column (5 µm particle size, 4.6×150 mm internal diameter) with a Phenomenex® SecurityGuard™ C18 guard column (3.0× 4.0 mm) was used to quantify the amount of tofacitinib in calibration samples, QC samples and tablets, performed on a Shimadzu HPLC system consisting of 2 LC-30AD pumps, a SIL-30AC autoinjector, a DGU-20A5 degasser and an SPD-20A UV detector (Shimadzu, Kyoto, Japan). Samples of 50 µL were injected into the Shimadzu HPLC system with the UV wavelength set at 287 nm and an isocratic method employed (mobile phase consisted of 50% v/v methanol in milli Q water with a flow rate of 1 mL/min and temperature controlled at 40° C.).

Results

Figure 8:
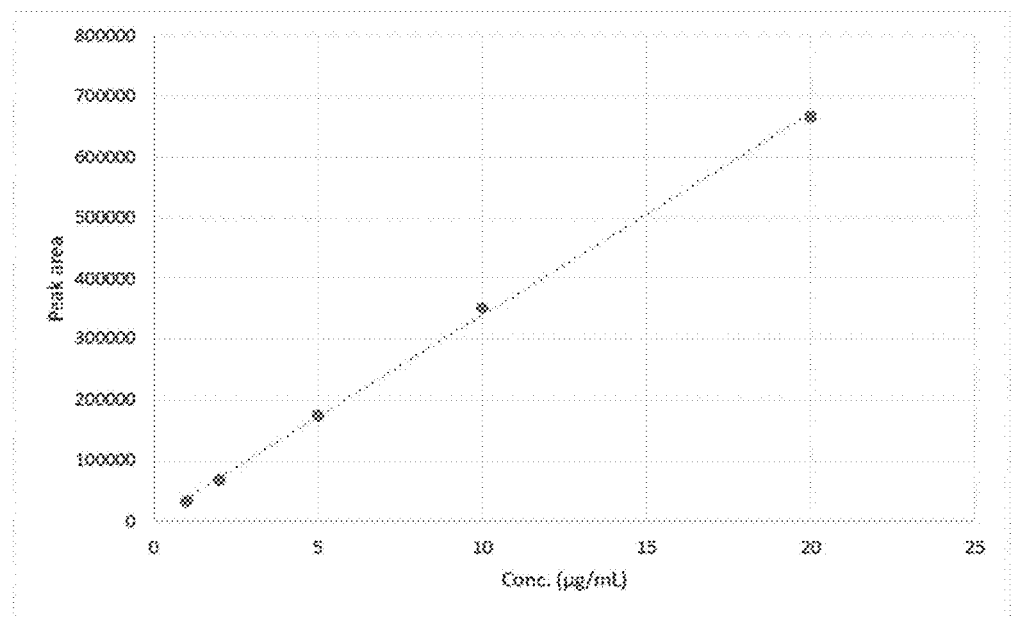
FIG. 8: A representative calibration curve of tofacitinib peak area over the tofacitinib concentration range of 1-20 μg/mL ($R^2$=0.9999, calculated by LabSolutions Version 5.82 SP1, Shimadzu Corporation, Kyoto, Japan).

HPLC assay validation: Under the conditions described above, the retention time of tofacitinib was 5.1 min. Chromatograms of blank solution (MeOH:$H_2O$=1:1), blank solution spiked with tofacitinib, and a tablet containing tofacitinib were prepared. A linear correlation between tofacitinib concentration and peak area of tofacitinib in MeOH:$H_2O$ (1:1) was observed over the range of 1 to 20 µg/mL ($R2$=0.9999), and a representative calibration curve is shown in FIG. 8. The precision and the accuracy values of the assay are shown in Table 8. The results demonstrated that the HPLC-UV method was robust and reliable for the quantification of tofacitinib in MeOH:$H_2O$ (1:1) over the concentration range of 1-20 µg/mL.

TABLE 8

Precision and accuracy of HPLC assay for quantification of tofacitinib in methanol:H2O (1:1)

| Target concentration (µg/mL) | Measured concentration (µg/mL) | Precision (%) Mean ± SD | Accuracy (%) |
|---|---|---|---|
| 1 | 0.86 ± 0.02 | 2.3 | 85.7 ± 2.0 |
| 20 | 20.04 ± 0.43 | 2.1 | 100.2 ± 2.1 |

Quantification of tofacitinib in tofacitinib citrate tablets: Using the developed assay, the amount of tofacitinib in each tablet was quantified and the results are shown in Table 9. Ranging from 5.0-5.6 mg, the amount of tofacitinib determined to be present in the 6 supplied tofacitinib citrate tablets was 5.4±0.3 mg (mean±SD).

TABLE 9

The measured amount of tofacitinib in individual tofacitinib citrate (5 mg) mini-tablets

| Tablet ID | Measured concentration (ug/mL) | Measured amount in the tablet (mg) | Measured amount (mg) Mean ± SD |
|---|---|---|---|
| 1 | 5.64 | 5.6 | 5.4 ± 0.3 |
| 2 | 5.59 | 5.6 | |
| 3 | 5.25 | 5.2 | |
| 4 | 5.59 | 5.6 | |
| 5 | 5.01 | 5.0 | |
| 6 | 5.21 | 5.2| | |

Conclusions

A HPLC-UV assay was developed to quantify tofacitinib in tofacitinib citrate tablets, which was robust and reliable over the concentration range of 1-20 µg/mL. Using this validated assay, the amount of tofacitinib determined to be present in 6 supplied tablets was 5.4±0.3 mg (mean±SD).

Example 4—Response of Alopecia Areata of the Beard to Oral Tofacitinib and Sublingual Tofacitinib Alopecia areata of the beard (BAA) affects 28% of men with alopecia areata (AA). In this study the records of male patients with scalp alopecia areata (SAA) who were treated for SAA with oral or sublingual tofacitinib at a specialist hair clinic between July 2016 and August 2019 were retrospectively reviewed. The inclusion criteria for this study were age ≥18 years, BAA and treatment with oral tofacitinib for ≥3 months. The Severity of Alopecia Tool (SALT) score was used to quantify scalp hair loss. Beard regrowth (none, partial or complete) was measured by an independent observer evaluation of global photographs. Data entry and analysis were performed using IBM SPSS Statistics v24.

Forty five patients met the inclusion criteria. The characteristics of the cohort are shown in table 10. Nineteen men had total beard loss, 24 had multiple discrete patches, and two had a solitary patch of BAA. Ten men achieved complete beard regrowth after 5.0-28.0 months of treatment (mean 16.0) (Table 11). The mean disease duration among complete beard responders was 93.2 months (range 12.0-252.0). 60% of men who achieved complete beard regrowth also achieved complete scalp hair regrowth. Of the 19 patients with partial beard regrowth, 15 achieved partial and one achieved complete scalp hair regrowth. Of 16 patients with no beard regrowth, 14 had no regrowth and two had partial regrowth of scalp hair.

Of the 45 patients, 21 were treated with oral tofacitinib and 24 were treated with sublingual tofacitinib (as described in Example 3). For patients receiving sublingual tofacitinib the doses were 2.5 mg, 5 mg, 7.5 mg, 8 mg, 10 mg or 10.5 mg. A comparison of the response to treatment with oral and sublingual tofacitinib is provided in Table 12. Patients treated were sublingual tofacitinib were more likely to have a partial or a complete response to treatment than patients treated with oral tofacitinib. A complete response was observed in 10 patients treated with sublingual tofacitinib and 0 patents treated with oral tofacitinib.

TABLE 10

Patient demographics and clinical characteristics (n = 45)

| Findings | N (%) | Mean ± SD | Median (Range) |
|---|---|---|---|
| Age (years) | | 38.6 ± 12.8 | 36.0 (20.0-67.0) |
| AA subtype: | | | |
| Solitary patch | 6 (13.3) | | |
| Multiple patches | 13 (28.9) | | |
| Diffuse | 8 (17.8) | | |
| AT | 4 (8.9) | | |
| AU | 14 (31.1) | | |
| SALT score pre-tofacitinib | | 62.0 ± 38.9 | 69.0 (2.0-100.0) |
| SALT score post-tofacitinib | | 41.7 ± 38.5 | 29.0 (0.0-100.0) |
| BAA subtype: | | | |
| Solitary patch | 2 (4.5) | | |
| Multiple patches | 24 (53.3) | | |
| Total beard loss | 19 (42.2) | | |
| Duration of BAA (months)† | | 61.2 ± 74.1 | 28.0 (3.0-324.0) |
| Dose of oral tofacitinib (mg) | | 7.2 ± 4.0 | 7.5 (1.0-20.0) |
| Duration of oral tofacitinib treatment (months) | | 15.5 ± 13.8 | 13.0 (3.0-86.0) |

TABLE 11

Response to treatment with oral tofacitinib (n = 45)

| | Degree of beard regrowth | | |
|---|---|---|---|
| | None | Partial | Complete |
| Number of patients (%) | 16 (35.6) | 19 (42.2) | 10 (22.2) |
| BAA subtype, N (%): | | | |
| Solitary patch | 2 (4.5) | 0 (0.0) | 0 (0.0) |
| Multiple patches | 8 (17.8) | 9 (20.0) | 7 (15.6) |
| Total beard loss | 6 (13.3) | 10 (22.2) | 3 (6.7) |
| Degree of scalp hair regrowth, N (%): | | | |
| None | 14 (31.1) | 3 (6.7) | 1 (2.2) |
| Partial | 2 (4.5) | 15 (33.3) | 3 (6.7) |
| Complete | 0 (0.0) | 1 (2.2) | 6 (13.3) |
| Duration of BAA (months), mean ± SD | 58.1 ± 78.5 | 45.1 ± 58.1 | 93.2 ± 72.5 |

TABLE 12

Comparison of the response to treatment with oral (N = 21) vs sublingual (n = 24) tofacitinib

| | Complete response | Partial response | No response |
|---|---|---|---|
| Sublingual | 10 | 7 | 7 |
| Oral | 0 | 12 | 9 |

There were no serious adverse events. Mild adverse events were seen in 10 patients and included upper respiratory infections, elevated liver transaminases, fatigue and acne. None required treatment cessation or dose modification.

Figure 9:
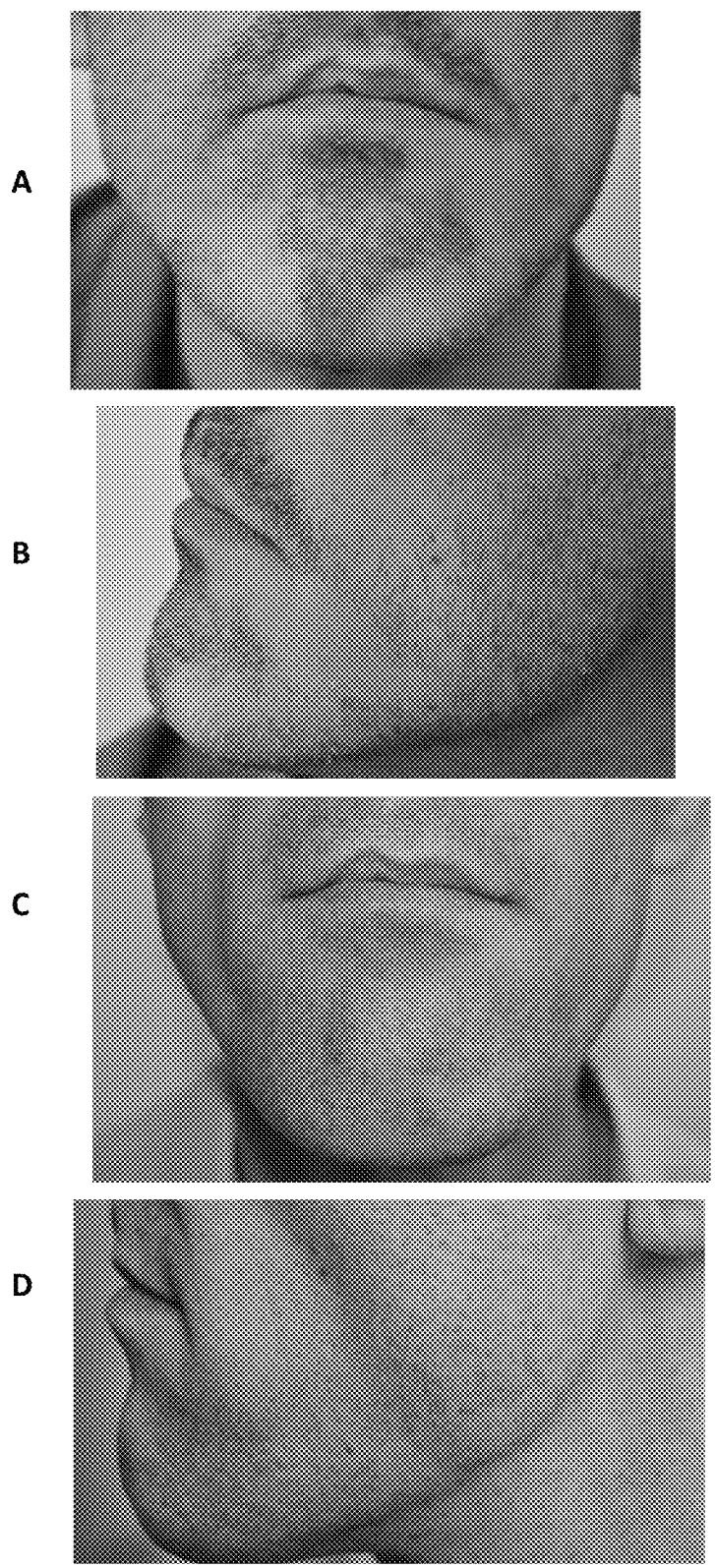
FIG. 9: Shows beard growth in a subject at baseline a) and b) and after treatment with sublingual tofacitinib c) and d).
Figure 10:
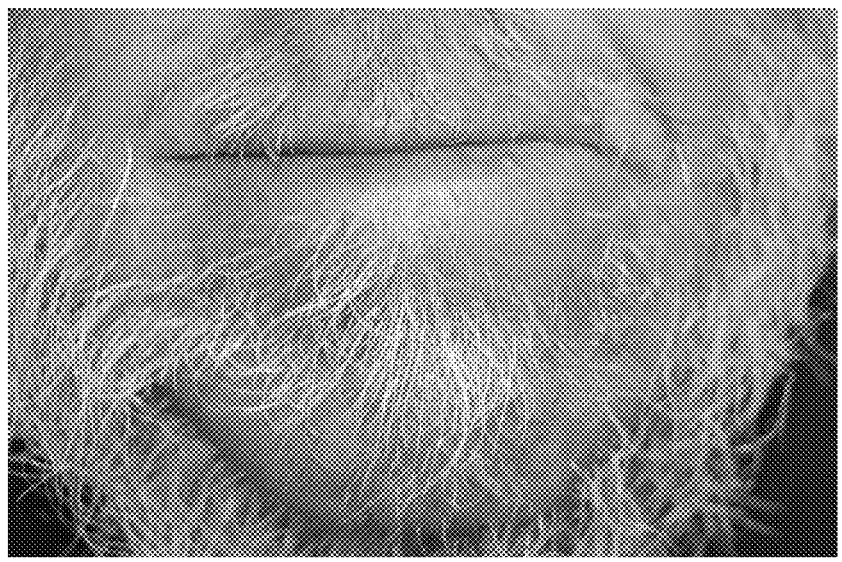
FIG. 10: Shows beard growth in a subject at baseline a) and after treatment with sublingual tofacitinib b).
Figure 10:
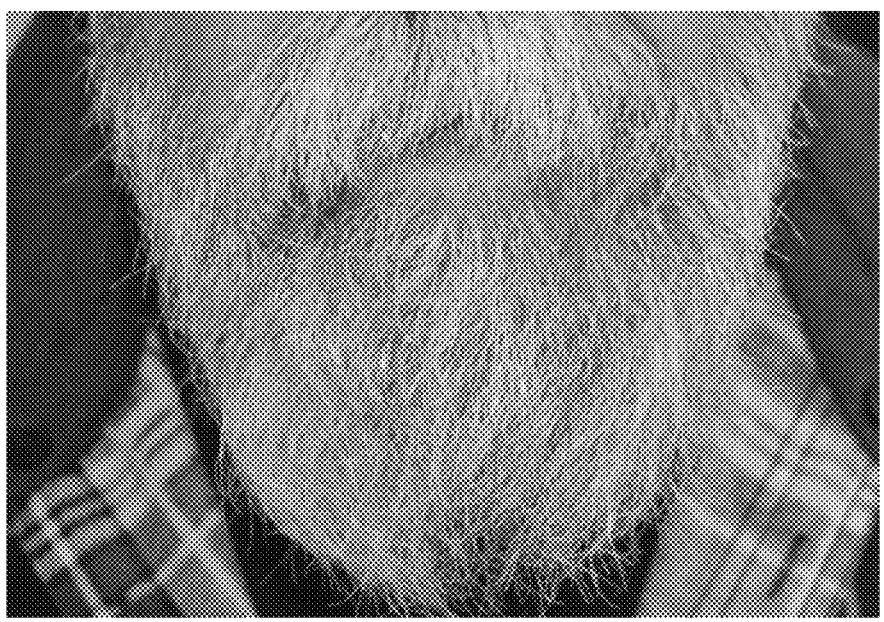

BAA is associated with a high prevalence of anxiety and depressive symptoms. Some religions e.g. Islam, Orthodox Judaism and Sikhism require adult males to grow a full beard. One patient in the study regularly competes in beard championships, and the loss of >50% of his beard as a result of BAA caused significant distress. The results of his treatment are shown in FIG. 10. A second representative Example of treatment is shown in FIG. 9.

In contrast to SAA studies which showed an inverse association between disease duration and treatment response, no such association was observed in BAA cohort in the current study. On the contrary, patients with complete beard regrowth had a longer mean disease duration. The age of the patient, BAA phenotype (patchy or total beard loss) and duration of treatment did not influence the degree of beard response. As with the BAA cohort, age did not predict improvement in SALT score in 90 patients with severe SAA treated with oral tofacitinib.

The findings indicate that sublingual tofacitinib is a therapeutic option for patients with BAA.

Example 5—Sublingual Tofacitinib for Lichen Planopilaris and Frontal Fibrosing Alopecia In a series of case studies sublingual tofacitinib has demonstrated activity at reducing the symptoms of the hair loss conditions lichen planopilaris and frontal fibrosing alopecia. The results of four cases studies are summarised below.

Patient 1: A 43 year-old male patient with lichen planopilaris with a previous history of lichen planus body. He tried multiple agents from 2015-2017 to control his condition including prednisolone, intralesional triamcinolone acetonide 5 mg/ml injections, clobetasol lotion, erythromycin, ciclosporin, simvastatin, minoxidil, and finasteride with no improvement. He commenced tofacitinib 1 mg twice daily February 2017. In view of intermittent activity, uptitrated to 5 mg twice daily. Activity of lichen planopilaris controlled from July 2019 until last review in February 2020 with sublingual tofacitinib 5-10 mg daily (as described in Example 3). Other concurrent meds of patient 1 were: finasteride 0.5 mg, minoxidil 5 mg, clarithromycin 250 mg daily, grapefruit extract 200 mg daily, topical clobetasol. No side effects were reported from tofacitinib.

Patient 2: A 46 year-old male with lichen planopilaris since 2011. Tried multiple treatments from June 2016-June 2017 including finasteride, minoxidil, plaquenil, ciclosporin, intralesional triamcinolone acetonide 5 mg/ml injections with no improvement. Commenced on tofacitinib 2.5 mg once daily June 2017; intermittent mild activity until June 2019; tofacitinib uptitrated to 5 mg once a day in the morning, 2.5 mg once a day at night at its peak; symptom-free in 20 Nov. 2019 (tofacitinib decreased to 2.5 mg once daily). Other concurrent meds of patient 2 were: finasteride 0.75 mg, minoxidil 4.5 mg, topical clobetasol. No side effects were reported from tofacitinib.

Patient 3: A 45 year-old female who first presented with lichen planopilaris and a 3-month history of patchy scarring alopecia on mid scalp with perifollicular scaling. Tried multiple treatments from May 2015-March 2017 including doxycycline, plaquenil, novasone lotion, intralesional triamcinolone acetonide 5 mg/ml injections, spironolactone, minoxidil, ciclosporin, prednisolone. Treatments did not improve the condition and were hair density reducing. Commenced on tofacitinib 2 mg twice daily, increased to 7.5 mg five months later. The patient was not happy with the response and ceased treatment at this time. Other concurrent medications of patient 3 include: spironolactone 100 mg, minoxidil 3.5 mg, and elocon lotion.

Patient 4: A 73 year-old female diagnosed to have co-existent lichen planopilaris/frontal fibrosing alopecia in 2013. Tried multiple treatments from 2013-2017 including: Intralesional triamcinolone acetonide 5 mg/ml injections, prednisolone, infrared light, plaquenil, ciclosporine, tetracyclines (minocycline and doxycycline), spironolactone, minoxidil with no improvement. Commenced on tofacitinib 2.5 mg twice daily. Treatment was continued for 12 months. The patient was not happy with the response and ceased treatment at this time. Concurrent meds of patient 4 were: minoxidil 5 mg, clarithromycin 250 mg daily and clobet lotion.

Sublingual tofacitinib was also observed to be useful for the treatment of data for treatment of folliculitis decalvans and tufted folliculitis in additional case studies (data not shown).

Example 6—the Combination of Sublingual Tofacitinib and Sublingual Minoxidil is Superior to Treatment with Sublingual Tofacitinib Alone in Subjects with Alopecia Areata Table 13 shows the mean salt score of prospective 18 months study in 16 patients with alopecia areata of the scalp treated with the combination of sublingual tofacitinib together with sublingual minoxidil. The mean change (reduction) in salt score was superior in the cohort treated with minoxidil and tofacitinib compared to the cohort treated with tofacitinib alone.

Table 13—Mean SALT score of prospective 18 months study in 16 patients who had sublingual tofacitinib together with sublingual minoxidil.

|  | Baseline | 3 months | 6 months | 9 months | 12 months | 18 months |
|---|---|---|---|---|---|---|
| Mean SALT score | 100 | 80 | 58 | 47 | 33 | 16 |

SALT 100 is total loss. Salt 0 is complete remission

REFERENCES

Almutairi and Nour (2019) Dermatology. 2019; 235(2):130-6.
Amin et al (2015) Oral film technology: Challenges and future scope for pharmaceutical industry 3(3): 183-203.
Bittencourt et al (2014) Clin Exp Dermatol 39:868-73.
Crispin et al (2016) JCI Insight. 1(15):e89776.
Dey and Maiti (2010) J Nat Sci Biol Med 1(1):2-5.
Dowty et al (2014) Drug metabolism and disposition: the biological fate of chemicals 42(4):759-73.
Gad et al (2008) Pharmaceutical manufacturing handbook: Production and processes. Published by Wiley-Interscience.
Irfan et al (2016) Saudi Pharmaceutical Journal 245:537-546.
Jabbari et al (2018) J Invest Dermatol. 2018; 138(7):1539-45.
Jamróz et al (2017) Int J Pharm. S0378-5173(17) 30464-7.
Lai et al (2019) Australas J Dermatol 60(1):e1-e13.
Lai et al (2019b). J Am Acad Dermatol (3):694-701.
Lamba et al (2016) Journal of clinical pharmacology 56(11): 1362-71.
Messenger and Sinclair (2006) Br J Dermatol 155: 926-930.
Messenger et al (2010) Eighth Edition. Blackwell Publishing. Oxford. 63.1-63.100.
Nagaraju et al (2013) Curr Drug Delivery 10(1):96-108.
Narang et al (2001) International Journal of Pharmacy and Pharmaceutical Sciences. 3(2):18-22.
Olsen et al (1997) Australas J Dermatol 38(20).
Olsen et al (1999) Journal of the American Academy of Dermatology. 1999; 40 (2 Pt 1):242-6.
Olsen et al (2004) Journal of the American Academy of Dermatology 51(3): p. 440-7.
Olsen et al (2016) Journal of the American Academy of Dermatology 75(6): p. 1268-1270.
Rowe et al (2009) Published by the Pharmaceutical Press and the American Pharmaceuticals Association.
Sayeed et al (2014) Pharmaceutical Technology. Volume 38, Issue 11.
Singh et al (2012) Journal of Drug Delivery 4:407-417.
Pfizer (2005) Medical Review application number: NDA 21-812 Minoxidil, Men's Rogaine extra strength 5% Topical foam.
Johnson & Johnson (2014) Product Monograph Submission control number: 1732017 Rogain Topical 2% solution.
USP/NP. Physical Tests: Disintegration (701) 22/17 ed. Rockville, MD: United States Pharmacopoeial Convention Inc; 1990

The invention claimed is:
1. A method of treating hair loss or excessive hair shedding in a subject or for promoting hair growth in a subject, the method comprising administering to the subject an effective dose of tofacitinib that is predominantly absorbed through the oral mucosa.

2. The method of claim 1, wherein the oral mucosa is the sublingual mucosa.

3. The method of claim 1, wherein the dose comprises a sublingual adhesion agent.

4. The method of claim 1, wherein tofacitinib is in the range of from about 0.1 mg to 50 mg, or from about 0.1 mg to 40 mg, or from about 0.1 mg to 30 mg, or of from about 0.1 mg to 20 mg, or from about 0.1 mg to 18 mg, or from about 0.1 mg to 15 mg, or from about 0.2 mg to 12.5 mg, or from about 0.2 mg to 10 mg, or from about 0.5 mg to 8 mg, or from about 1 mg to 6 mg, or from about 1 mg to 5 mg, or from about 1 mg to 4 mg, or from about 1 mg to 3 mg, or from about 1 mg to 2 mg, or is about 10 mg, or is about 8 mg, or is about 7.5 mg, or is about 5 mg, or is about 4 mg, or is about 3 mg, or is about 2.5 mg, or is about 2 mg, or is about 1 mg, or is about 0.5 mg daily.

5. The method of claim 1, wherein the dose is administered at least every 3 days, at least every 2 days, or daily.

6. The method of claim 1, wherein the dose is in a form selected from a: strip, wafer, pellet, film, troche, tablet, lipid matrix tablet, capsule, pill, granule, pellet, powder, drop, spray and lozenge.

7. The method of claim 1, which further comprises administering one or more of a: (i) vasodilator, (ii) aldosterone antagonist, (iii) 5α-reductase inhibitor, (iv) nonsteroidal antiandrogen drug, (v) steroidal antiandrogen, (vi) prostaglandin $D_2$ receptor antagonist, (vii) immunosuppressant, and (viii) glucocorticoid.

8. The method of claim 1, which further comprises administering one or more of:
(i) minoxidil in the range of from about 0.1 mg to 20 mg;
(ii) spironolactone in the range of from about 10 mg to 500 mg;
(iii) finasteride in the range of from about 0.1 mg to 1 mg;
(iv) dutasteride in the range of from about 0.01 mg to 1 mg;
(v) flutamide in the range of from about 10 mg to 500 mg;
(vi) cyproterone acetate in the range of from about 1 mg to 100 mg;
(vii) bicalutamide in the range of from about 1 mg to 100 mg;
(viii) enzalutamide in the range of from about 1 mg to 100 mg;
(ix) nilutamide in the range of from about 1 mg to 100 mg;
(x) drosperidone in the range of from about 0.1 mg to 10 mg;
(xi) apalutamide in the range of from about 1 mg to 100 mg;
(xii) buseralin in the range of from about 0.1 mg to 10 mg;
(xiii) setipiprant in the range of from about 50 mg to 4000 mg;
(xiv) fevipiprant in the range of from about 50 mg to 1000 mg;
(xv) cyclosporin in the range of from about 10 mg to 600 mg;
(xvi) methotrexate in the range of from about 2.5 mg to 40 mg;
(xvii) azathioprine in the range of from about 25 mg to 200 mg;
(xviii) prednisolone in the range of from about 0.1 mg to 40 mg; and
(xix) dexamethasone in the range of from about 0.1 mg to 5 mg.

9. The method of claim 1, wherein the hair loss or excessive hair shedding is the result of one or more of the following autoimmune conditions: alopecia areata, alopecia totalis, alopecia universalis, androgenetic alopecia, telogen effluvium, anagen effluvium, male pattern baldness, female pattern baldness, monilethrix, anaemia, polycystic ovary syndrome, cicatricial alopecia, loose anagen hair syndrome, folliculitis decalvans, frontal fibrosing alopecia, tufted folliculitis, alopecia planopilaris, frontal fibrosing alopecia, lichen planopilaris, lichen frontal fibrosing, and treatment resistant alopecia areata.

10. The method of claim 1, wherein promoting hair growth comprises promoting beard growth in the subject and/or comprises increasing hair length in the subject.

11. An oral composition comprising tofacitinib, wherein the composition is predominantly absorbed through the oral mucosa for treating hair loss or excessive hair shedding in a subject or for promoting hair growth in a subject.

12. The composition of claim 11, wherein the oral composition is a sublingual composition predominantly absorbed through the sublingual mucosa.

13. The composition of claim 11, wherein tofacitinib is in the range of from about 0.1 mg to 50 mg, or from about 0.1 mg to 40 mg, or from about 0.1 mg to 30 mg; or from about 0.1 mg to 20 mg, or from about 0.1 mg to 18 mg, or from about 0.1 mg to 15 mg, or from about 0.2 mg to 12.5 mg, or from about 0.2 mg to 10 mg, or from about 0.5 mg to 8 mg, or from about 1 mg to 6 mg, or from about 1 mg to 5 mg, or from about 1 mg to 4 mg, or from about 1 mg to 3 mg, or from about 1 mg to 2 mg, or is about 5 mg, or is about 4 mg, or is about 3 mg, or is about 2 mg, or is about 1 mg, or is about 0.5 mg daily.

14. The composition of claim 11, which additionally comprises one or more of:
(i) minoxidil in the range of from about 0.1 mg to 20 mg;
(ii) spironolactone in the range of from about 10 mg to 500 mg;
(iii) finasteride in the range of from about 0.1 mg to 1 mg;
(iv) dutasteride in the range of from about 0.01 mg to 1 mg;
(v) flutamide in the range of from about 10 mg to 500 mg;
(vi) cyproterone acetate in the range of from about 1 mg to 100 mg;
(vii) bicalutamide in the range of from about 1 mg to 100 mg;
(viii) enzalutamide in the range of from about 1 mg to 100 mg;
(ix) nilutamide in the range of from about 1 mg to 100 mg;
(x) drosperidone in the range of from about 0.1 mg to 10 mg;
(xi) apalutamide in the range of from about 1 mg to 100 mg;
(xii) buseralin in the range of from about 0.1 mg to 10 mg;
(xiii) setipiprant in the range of from about 50 mg to 4000 mg;
(xiv) fevipiprant in the range of from about 50 mg to 1000 mg;
(xv) cyclosporin in the range of from about 10 mg to 600 mg;
(xvi) methotrexate in the range of from about 2.5 mg to 40 mg;
(xvii) azathioprine in the range of from about 25 mg to 200 mg;
(xviii) prednisolone in the range of from about 0.1 mg to 40 mg; and
(xix) dexamethasone in the range of from about 0.1 mg to 5 mg.

15. The composition of claim 11, wherein the composition comprises one or more of:
  (i) a sublingual adhesion agent;
  (ii) a disintegration agent which aids disintegration of the composition in the presence of saliva;
  (iii) a taste modifying agent; and
  (iv) an elimination half-life of about 3 to 12 hours.

16. The composition of claim 11, wherein the composition is in a form selected from a: strip, wafer, pellet, film, troche, tablet, lipid matrix tablet, capsule, pill, granule, pellet, powder, drop, spray and lozenge.

17. A composition that is predominantly absorbed through the oral mucosa for treating hair loss or excessive hair shedding in a subject or for promoting hair growth in a subject, the composition comprising tofacitinib and minoxidil.

18. The composition of claim 17, wherein the composition is predominantly absorbed through the sublingual mucosa.

* * * * *